United States Patent
Cox et al.

(10) Patent No.: US 8,603,753 B2
(45) Date of Patent: Dec. 10, 2013

(54) IMMUNOASSAY FOR DETECTION OF NEUROTOXIC AMINO ACID ASSOCIATED WITH NEUROLOGICAL DISORDERS

(75) Inventors: Paul Alan Cox, Jackson, WY (US); James S. Metcalf, Dundee (GB); Geoffrey A. Codd, Longforgon (GB)

(73) Assignees: The Institute for Ethnomedicine, Provo, UT (US); The University of Dundee, Scotland (GB)

( * ) Notice: Subject to any disclaimer, the term of this patent is extended or adjusted under 35 U.S.C. 154(b) by 75 days.

(21) Appl. No.: 13/056,877

(22) PCT Filed: Jul. 2, 2009

(86) PCT No.: PCT/US2009/049581
§ 371 (c)(1),
(2), (4) Date: May 25, 2011

(87) PCT Pub. No.: WO2010/014349
PCT Pub. Date: Feb. 4, 2010

(65) Prior Publication Data
US 2011/0223624 A1 Sep. 15, 2011

Related U.S. Application Data

(60) Provisional application No. 61/079,334, filed on Jul. 9, 2008.

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

U.S. PATENT DOCUMENTS

| | | |
|---|---|---|
| 4,762,781 A | 8/1988 | Geffard |
| 2007/0292893 A1 | 12/2007 | Cox et al. |

FOREIGN PATENT DOCUMENTS

WO  WO 01/18059 A2  3/2001

OTHER PUBLICATIONS

Campbell (Monoclonal antibody technology 1986 Elsevier Science Publisher, p. 1-28).*
Carmichael et al., Human Fatalities from Cyanobacteria: Chemical and Biological Evidence for Cyanotoxins, Environ health Perspect., 2001, 109:663-668.
Collings et al., Novel Technologies for the Discovery and Quantitation of Biomarkers of Toxicity, Toxicology, 2008, 245:167-174.
Thiel et al., Effect on Heterocyst Differentiation of Nitrogen Fixation in Vegetative Cells of the Cyanobacterium Anabaena variabilis ATCC 29413, J. Bacteriol., 2001, 183:280-286.
Velthuis et al., In vivo Antinuclear Antibody of the Skin: Diagnostic Significance and Association with Selective Antinuclear Antibodies, Annals of the Rheumatic Diseases, 1990, 49:163-167.
Lawton, L., et al., Chapter 23: Conventional Laboratory Methods for Cyanotoxins, Advances in Experimental Medicine and Biology Springer-Verlag, Berlin, Heidelberger Platz 3, D-14197 Berlin, Germany Series: Advances in Experimental Medicine and Biology 2008, pp. 513-537 & International Symposium on Cyanobacterial Algal Blooms—State of the Science and Research Needs; Research Triangle Park, NC, USA, Sep. 6-10, 2005.
European Application No. 09803340.0, Extended European Search Report dated Aug. 19, 2011.

* cited by examiner

*Primary Examiner* — Jacob Cheu
(74) *Attorney, Agent, or Firm* — Pillsbury Winthrop Shaw Pittman LLP

(57) ABSTRACT

An immunoassay for screening a sample to detect the presence of β-N-methylamino-L-alanine (BMAA) is disclosed. Antibodies specific for BMAA are disclosed. Antibodies that bind to BMAA on immunoblots are disclosed. Immunoassays and kits to detect the presence of BMAA in a sample by contacting the sample with an antibody that binds to BMAA, and detecting the antibody bound to the sample, are disclosed. Immunoassays and kits for screening for the presence of BMAA in a subject by analyzing a tissue sample obtained from the subject to detect the present of BMAA in the tissue sample, where the presence of BMAA in the tissue sample indicates exposure of the subject to an environmental source of BMAA, are disclosed. Immunoassays and kits for detecting an environmental source of BMAA, by screening an environmental sample to detect the presence of BMAA in the sample, wherein the presence of a detectable amount of BMAA in the sample indicates the sample is an environmental source of BMAA, are disclosed.

42 Claims, 7 Drawing Sheets

IMMUNOASSAY FOR DETECTION OF NEUROTOXIC AMINO ACID ASSOCIATED WITH NEUROLOGICAL DISORDERS

CROSS-REFERENCE TO RELATED APPLICATIONS

This is the U.S. National Stage of PCT/US2009/049581, filed Jul. 2, 2009, which in turn claims priority to U.S. Provisional Patent Application No. 61/079,334, filed Jul. 9, 2008, the entire contents of all of which are incorporated herein by reference in their entireties.

RELATED APPLICATIONS

This application claims the benefit of priority of provisional application Ser. No. 61/079,334, filed Jul. 9, 2008, which is expressly incorporated herein by reference in its entirety.

FIELD OF THE INVENTION

The present invention relates to antibodies that bind to β-N-methylamino-L-alanine (BMAA), and immunoassays and kits for screening samples to detect the presence of BMAA in the samples.

BACKGROUND OF THE INVENTION

The non-protein amino acid β-N-methylamino-L-alanine (BMAA) is produced by diverse taxa of cyanobacteria (Cox et al. (2005) *Proc Natl Acad Sci USA* 102: 5074-5078) and has been shown to have neuroexcitatory and neurotoxic effects when administered in vivo and in vitro under various experimental conditions. Because BMAA can be found in flour made from cycad seeds, BMAA has been considered a candidate neurotoxin associated with a unique neurological disease identified decades ago among the Chamorro people of Guam, known as amyotrophic lateral sclerosis-Parkinsonism dementia complex of Guam (ALS-PDC) because of the combination of symptoms having clinical similarity to features of amyotrophic lateral sclerosis (ALS), Parkinsonism, and dementias, where occurrence of the disease has been linked with a diet that includes BMAA-containing cycad flour. (inter alia, Spencer et al. (1987) *Science* 237:517-522; Kisby et al. (1992) *Neurodegeneration* 1:73-82). Biomagnification of BMAA in food chains has been demonstrated, e.g. in Guam, where BMAA produced by cyanobacterial symbionts in cycad roots is taken up by the cycad host and accumulated in structures such as the seed sarcotesta and seed gametophyte that are eaten by flying foxes (bats) or people that further accumulate BMAA in their tissues, with a dramatic biomagnification seen when flying foxes (bats) with high accumulated levels of BMAA are eaten by people. (inter alia, Bannack et al. (2003) *Neurology* 61387-389; Cox et al. (2002) *Neurology* 58: 956-959; Cox et al. (2003) *Proc Natl Acad Sci USA* 100:13380-13383).

Recently, BMAA has since been detected in tissues of subjects who have not eaten cycads or flying foxes, where some subjects with detectable levels of BMAA had clinical diagnoses (based on symptoms) or confirmed diagnoses (e.g., based on autopsy of brain tissue) of neurological disorders such as Alzheimer's disease, ALS, and progressive supranuclear palsy (PSP), while other subjects with detectable levels of BMAA were asymptomatic for neurological disorders. (Cox et al. (2003) *Proc Natl Acad Sci USA* 100:13380-1338; Murch et al. (2004) *Proc Natl Acad Sci USA* 101: 12228-12231; Murch et al. (2004) *Acta Neurol Scand* 110: 267-269; U.S. Pat. No. 7,256,002; US Publication No. 20070254315; US Publication No. 20070292893)

Chromatographic methods for analyzing tissue samples and environmental samples for neurotoxic amino acids such as BMAA, by high performance liquid chromatography (HPLC) or HPLC-mass spectroscopy (HPLC-MS) analysis of tissue samples and/or environmental samples is disclosed (Cox et al. (2003) *Proc Natl Acad Sci USA* 100:13380-1338; Murch et al. (2004) *Proc Natl Acad Sci USA* 101: 12228-12231; Murch et al. (2004) *Acta Neurol Scand* 110:267-269; U.S. Pat. No. 7,256,002; US Publication No. 20070254315)

SUMMARY OF THE INVENTION

The present invention provides an immunoassay for screening a sample to detect the presence of β-N-methylamino-L-alanine (BMAA). The present invention provides an immunoassay wherein free BMAA is detected, or wherein protein-bound BMAA is detected, or wherein both free BMAA and protein-bound BMAA is detected. The immunoassay as provided herein can be an enzyme-linked immunosorbent assay (ELISA), where the ELISA can be, but is not limited to, an antibody capture assay, an indirect competitive ELISA, or a direct ELISA. The immunoassay provided herein may be an immunoblot assay.

The present invention provides an immunoassay for screening a sample to detect the presence of BMAA, wherein the immunoassay includes an antibody that binds to BMAA. The present invention provides an immunoassay for screening a sample to detect the presence of BMAA, that includes an antibody that binds to BMAA and does not substantially bind to an amino acid selected from the group consisting of L-alanine, L-glutamine, L-tyrosine, glycyl-glycine, L-glycine, L-leucine, L-phenylalanine, gamma-aminobutyric acid (GABA), L-glutamic acid, and L-aspartic acid. The present invention provides an immunoassay that includes an antibody that binds to BMAA, wherein the antibody can be a polyclonal antibody, a monoclonal antibody, or an antibody fragment. The present invention provides an immunoassay that includes an antibody that binds to BMAA, wherein the antibody can be detectably labelled, wherein the label can be, but is not limited to, a radiolabel, a fluorescent moiety, a luminescent moiety, a chemiluminescent moiety, a colloidal gold label, a dye moiety, a paramagnetic compound, a detectable enzyme, biotin, avidin, or streptavidin. The present invention provides an immunoassay that includes an antibody that binds to BMAA, wherein the antibody can be an antibody that is not detectably labelled, and wherein the immunoassay further includes a detectably labelled secondary antibody that binds to the unlabelled antibody that binds to BMAA, wherein the label can be, but is not limited to, a radiolabel, a fluorescent moiety, a luminescent moiety, a chemiluminescent moiety, a colloidal gold label, a dye moiety, a detectable enzyme, a detectable ligand, biotin, avidin, or streptavidin. The secondary antibody can be labelled with horseradish peroxidase (HRP).

The present invention provides an immunoassay for screening a sample to detect the presence of BMAA, wherein the immunoassay further includes an amplification step.

The present invention provides methods for screening a sample to detect the presence of BMAA using an immunoassay as provided herein, by contacting the sample with an antibody that binds to BMAA, and detecting the antibody. The present invention provides methods for screening a tissue sample from a subject to detect the presence of BMAA in the tissue sample, using an immunoassay as provided herein, wherein the presence of a detectable amount of BMAA in the sample indicates exposure of the subject to an environmental source of BMAA. The present invention provides methods for screening a sample to detect the presence of BMAA in tissue samples including, but not limited to neurological tissue or non-neurological tissue, where neurological tissue can be keratinous tissue such as hair, skin, nail, claw, or hoof. The present invention provides methods for screening a sample to detect the presence of BMAA using an immunoassay as provided herein, by detecting protein-bound BMAA on an immunoblot of the tissue sample. The present invention provides methods for screening an environmental sample to detect the presence of BMAA in the environmental sample, using an immunoassay as provided herein, wherein the environmental sample can be, but is not limited to, a water sample or a sample from a food item. The present invention provides methods for screening an environmental sample to detect the presence of BMAA in the environmental sample, using an immunoassay as provided herein, wherein the methods can further include screening the sample to detect cyanobacterial material in the sample. The present invention provides methods for screening an environmental sample by detecting the presence of protein-bound BMAA on an immunoblot of the environmental sample, and further detecting cyanobacterial proteins on the immunoblot.

The present invention provides an antibody that binds to BMAA. The present invention provides an antibody that binds to BMAA and does not substantially bind to an amino acid selected from the group consisting of L-alanine, L-glutamine, L-tyrosine, glycyl-glycine, L-glycine, L-leucine, L-phenylalanine, gamma-aminobutyric acid (GABA), L-glutamic acid, or L-aspartic acid. The present invention provides an antibody that binds to BMAA, wherein the antibody can binds to free BMAA, or wherein the antibody binds to protein-bound BMAA, or wherein the antibody binds to both free BMAA and protein-bound BMAA. The present invention provides an antibody that binds to BMAA, wherein the antibody binds to the L-BMAA isomer and does not substantially bind the D-isomer of BMAA. An antibody that binds to BMAA as provided herein can be a polyclonal antibody, or a monoclonal antibody, or an antibody fragment. An antibody that binds to BMAA as provided herein can be detectably labelled. An antibody that binds to BMAA as provided herein can be labelled for use in in vivo diagnostic imaging.

The present invention provides kits for screening a sample to detect the presence of BMAA, where the kit includes a carrier means (carrier) that is compartmentalized to receive one or more container means (containers), and the kit includes at least one container means with an antibody that binds to BMAA. In kits as provided herein, an antibody that binds to BMAA can be detectably labelled, and kits can further include at least one container means (container) with means for detecting the labelled antibody bound to the sample. In kits as provided herein, an antibody that binds to BMAA can be unlabelled, and can further include at least one container means with a labelled secondary antibody that binds to the unlabelled antibody, and can further include a container means with means for detecting the labelled secondary antibody bound to the unlabelled antibody bound to the sample. Kits as provided herein can include a container means with a control sample containing a known amount of BMAA. Kits as provided herein can include means for preparing the sample to detect the presence of BMAA, where such means may include, but are not limited to, means for mechanically disrupting the sample and means for chemically disrupting the sample. The present invention provides kits for screening a tissue sample from a subject to detect the presence of BMAA, where the tissue sample can be, but is not limited to, a keratinous tissue sample such as hair or skin. The present invention provides kits for screening an environmental sample to detect the presence of BMAA, wherein the environmental sample can be, but is not limited to, a water sample or a sample from a food item. Kits as provided herein can contain means for screening a plurality of sample types.

Lane 3, BSA probed with anti-KGB antiserum at 1/200 dilution; Lane 4, CR3 protein probed with anti-KGB antiserum at 1/200 dilution; Lane 5, BSA probed with anti-KGB antiserum at 1/500 dilution; Lane 6, CR3 protein probed with anti-KGB antiserum at 1/500 dilution; Lane 7, BSA probed with anti-KGB antiserum at 1/1000 dilution; Lane 8, CR3 protein probed with anti-KGB antiserum at 1/1000 dilution; Lane 9, BSA probed with anti-KGB antiserum at 1/2000 dilution; Lane 10, CR3 protein probed with anti-KGB antiserum at 1/2000 dilution; Lane 12, CR3 protein probed with null serum at 1/200 dilution; Lane 13, BSA probed with anti-KEB antiserum at 1/200 dilution; Lane 14, CR3 protein probed with anti-KEB antiserum at 1/200 dilution; Lane 15, BSA probed with anti-KEB antiserum at 1/500 dilution; Lane 16, CR3 protein probed with anti-KEB antiserum at 1/500 dilution; Lane 17, BSA probed with anti-KEB antiserum at 1/1000 dilution; Lane 18, CR3 protein probed with anti-KEB antiserum at 1/1000 dilution; Lane 19, BSA probed with anti-KEB antiserum at 1/2000 dilution; and Lane 20, CR3 protein probed with anti-KEB antiserum at 1/2000 dilution.

Figure 7:
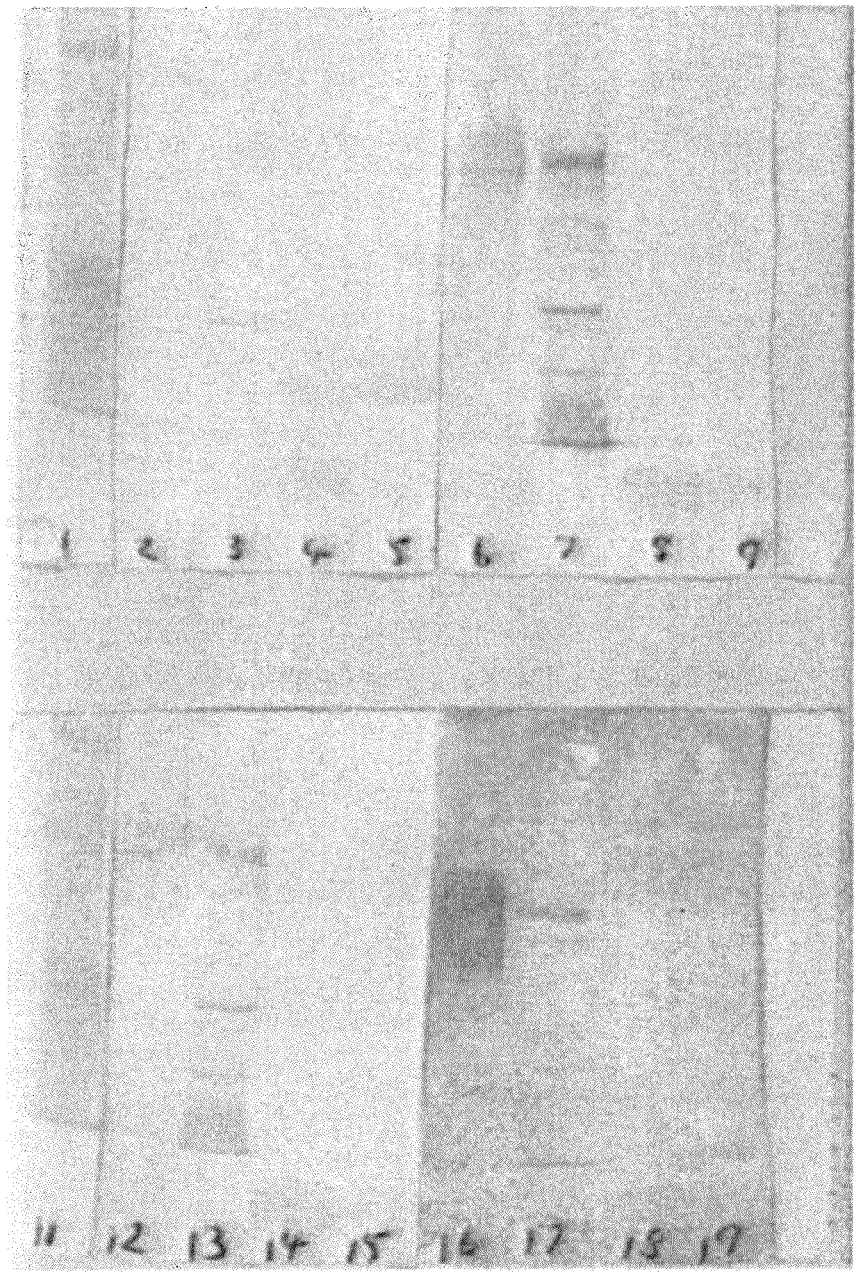

FIG. 7 shows an image of an immunoblot of total protein extracts (20 µg protein per lane) of pure strains of *Cylindrospermopsis raciborskii* strain CR3 ("CR3 protein"), *E. coli* strain HK29 ("*E. coli* HK 29 protein"), *Chlorella vulgaris* ("*Chlorella* protein") and *Tetraselmis* sp. ("*Tetraselmis* protein") probed with antisera raised against BMAA conjugates, where Lanes 1 and 11 contain molecular weight markers (100-1000 Da), Lanes 2, 6, 12, and 16 contain CR3 protein, Lanes 3, 7, 13, and 17 contain *E. coli* HK29 protein; Lanes 4, 8, 14, and 18 contain *Chlorella* protein, and Lanes 5, 9, 15, and 19 contain *Tetraselmis* protein, and Lanes 2-5 were probed with null serum at 1/500 dilution, Lanes 6-9 were probed with anti-KEB antiserum at 1/500 dilution, Lanes 12-15 were probed with anti-KEB antisera at 1/1000 dilution, and Lanes 16-19 were probed with anti-KGB antisera at 1/500 dilution.

DETAILED DESCRIPTION OF THE INVENTION

The present disclosure provides immunoassays, antibodies, and kits for screening samples to detect neurotoxic amino acids associated with neurological disorders. The present invention provides immunoassays, antibodies, and kits to detect the presence of BMAA in a sample, comprising contacting the sample with an antibody that binds to BMAA, and detecting the antibody bound to the sample. Immunoassays, antibodies, and kits are provided to screen samples to detect β-N-methylamino-L-alanine (BMAA) in the samples. Immunoassays, antibodies, and kits are provided to screen a subject to detect exposure to an environmental source of BMAA. Immunoassays, antibodies, and kits are provided to screen environmental samples to identify environmental sources of BMAA.

The present invention provides immunoassays, antibodies, and kits to detect the presence of BMAA in a tissue sample from a subject by contacting the tissue sample with an antibody that binds to BMAA, and detecting the antibody bound to the tissue sample. In accordance with one aspect of the invention, immunoassays, antibodies, and kits are provided for screening a subject for exposure to an environmental source of BMAA using an immunoassay of the invention to detect BMAA in a tissue sample from the subject, wherein the presence of a detectable amount of BMAA in the tissue sample indicates the subject has been exposed to an environmental source of BMAA, such that BMAA has accumulated to a detectable level in the tissue being screened. In accordance with another aspect of the invention, immunoassays, antibodies, and kits are provided for screening a subject for exposure to a neurotoxic amino acid associated with neurological disorders, in particular BMAA, using an immunoassay of the invention to detect BMAA in a tissue sample from the subject, wherein the presence of a detectable amount of BMAA in the tissue sample indicates the subject has been exposed to a neurotoxic amino acid associated with neurological disorders. In accordance with another aspect of the invention, immunoassays, antibodies, and kits are provided for screening a subject having or at risk of having a neurological disease, using an immunoassay of the invention to detect BMAA in a tissue sample from the subject.

The present invention provides immunoassays, antibodies, and kits to determine the presence of BMAA in an environmental sample by contacting the environmental sample with an antibody that binds to BMAA, and detecting the antibody bound to the environmental sample. In accordance with one aspect of the invention, immunoassays, antibodies, and kits are provided for screening for an environmental source of BMAA using an immunoassay of the invention to detect BMAA in the environmental sample, wherein the presence of a detectable amount of BMAA in an environmental sample indicates the sample is an environmental source of BMAA. In accordance with another aspect, immunoassays, antibodies, and kits are provided for screening environmental samples for neurotoxic amino acids associated with neurological disorders, in particular BMAA. In one embodiment, the present invention provides an immunoassay for detecting the presence of BMAA in environmental samples that may be, or have been, ingested by a subject. In one embodiment, the environmental samples may include, but are not limited to, water samples or food items.

Unless defined otherwise, all technical and scientific terms used herein has the meaning commonly understood by a person skilled in the art to which this invention belongs. Although any methods and materials similar or equivalent to those described herein can be used in the practice or testing of the present invention, non-limiting exemplary embodiments of methods and materials are described herein.

Although the term "antibody" or "antibodies" is understood to originally refer to a polypeptide substantially encoded by an immunoglobulin gene or fragments thereof, that specifically binds and recognizes an antigen target, the term "antibody" or "antibodies" as used herein encompasses immunoglobulins, immunoglobulin fragments, intact antibodies, polyclonal antibodies, monoclonal antibodies, sera reactive against an antigen (i.e., antisera raised against an antigen), antibodies produced by expression of endogenous genetic sequences, recombinant antibodies, humanized antibodies, chimeric antibodies, synthetic antibodies (synthesized de novo), multivalent antibodies, single chain antibodies, antibody fragments, antibody subsequences, any antibody portion that retains capacity to bind antigen, monovalent Fab fragments, bivalent F(ab')2 fragments, Fd fragments, dAb fragments, Fv fragments (variable fragments), single chain Fv fragments (scFvs), isolated complementarity determining regions (CDRs), epitope binding polypeptides generated using phage display libraries, etc., where more than one of the terms listed above may be used to describe an antibody of the invention, e.g., a recombinant monoclonal antibody that binds BMAA.

The phrase "detect the presence of BMAA" or "detecting the presence of BMAA" or a similar phrase or grammatical equivalent thereof, encompasses determining the presence or absence of a detectable level or amount of BMAA in a sample, and is understood to generally encompass determining or quantifying the level or amount of BMAA in a sample.

It is understood that the phrase is used in a non-limiting manner. Further, the phrase "determine BMAA levels" or "determining BMAA levels" or a similar phrase, is understood to encompass determining or quantifying the level or amount of BMAA in a sample. In certain non-limiting embodiments, immunoassays are provided that only confirm the presence or absence of a detectable level of BMAA is present in the sample. In certain non-limiting embodiments, immunoassays are provided that provide means for determining or quantifying the level or amount of BMAA in a sample or sample fraction. In other non-limiting embodiments, immunoassays are provided that permit analysis and comparison of multiple samples, e.g. to determine whether the level of BMAA in one sample is elevated or decreased in comparison with the levels detected in other samples.

"Screen" or "screening" or a similar phrase as used herein includes, but is not limited to screening to detect the presence of neurotoxic amino acids associated with neurological disorders and screening to determine the level or amount of neurotoxic amino acid, and encompasses screening a tissue sample from a subject to determine actual or potential exposure of a subject to neurotoxic amino acids associated with neurological disorders, in particular BMAA, and screening to identify environmental samples containing neurotoxic amino acids associated with neurological disorders, in particular BMAA.

"Binding specificity" or "specific binding" refers to the substantial recognition of, and substantial binding to, a first molecule for a second molecule. The invention provides antiserum raised against BMAA conjugated to carrier proteins (anti-BMAA antiserum) having the capacity for substantial recognition of, and substantial binding to, BMAA, i.e., anti-BMAA antiserum having binding specificity for, and specific binding to, BMAA. The present invention provides antibodies having binding specificity for and specific binding to BMAA, wherein an antibody of the present invention includes but is not limited to, a polyclonal antibody, a monoclonal antibody, or an antibody fragment, e.g., a Fv, single chain Fv, Fab', or F(ab')2 fragment, having binding specificity for BMAA.

The phrase "substantial binding" or "substantially bind" or a similar phrase, as used herein, refers to an amount of specific binding or recognizing or reactivity between molecules in an assay mixture under particular assay conditions. As used herein, substantial binding relates to the difference between an antibody's capability of binding or recognizing BMAA (target molecules), and the antibody's lack of capability of binding one or more different molecules, e.g., amino acids that are structurally similar to BMAA (non-target molecules), such that the difference is sufficient to allow a meaningful assay for detecting BMAA to be conducted under a particular set of assay conditions. Assay conditions that may affect binding or reactivity between molecules include, but are not limited to, the relative concentrations of the target and non-target molecules, and the time and temperature of an incubation. Likewise, substantial binding relates to the difference between an antibody's reactivity with BMAA, and the antibody's lack of reactivity with one or more different molecules, e.g., amino acids that are structurally similar to BMAA, such that the difference is sufficient to allow a meaningful assay for detecting BMAA to be conducted under a particular set of assay conditions. The phrase "does not substantially bind" or "does not substantially cross-react" as used herein, generally refers to an amount of binding or recognizing between molecules in an assay mixture under particular assay conditions wherein an antibody capable of binding or recognizing BMAA is substantially incapable of binding or recognizing another molecule such as a structurally similar amino acid, i.e., an antibody capable of binding or recognizing BMAA is substantially incapable of cross-reacting with other molecules such as structurally similar amino acids. An antibody having reactivity with BMAA may have a binding capacity or cross-reactivity with structurally similar amino acids that is less than 25%, preferably less than 10%, more preferably less than 5% of the reactivity exhibited toward BMAA under a particular set of assay conditions, which includes the relative concentration and incubation of the molecules. An antibody having reactivity with BMAA that "does not substantially bind" structurally similar amino acids may show detectable binding to structurally similar amino acids, or may not show detectable binding to structurally similar amino acids under a particular set of assay conditions. Specific binding, substantial binding, or lack of substantial binding, can be tested using a number of widely known methods, e.g., an enzyme-linked immunosorbent assay (ELISA), in particular antibody capture ELISA or indirect competitive ELISA, or an immunoblot ("Western blot") assay, or a radioimmunoassay (RIA), or an immunohistochemical assay.

As provided herein, a subject may be any organism suitable for practicing the methods of the present invention. In particular, a subject is a mammal, more particularly a primate, even more particularly a human. In one embodiment, a subject is an experimental animal that is exposed to a neurotoxic amino acid or neurotoxic derivative thereof associated with neurological disorders. Such experimental animals include, but are not limited to, a mouse, rabbit, rat, bat, pig, sheep, cow, monkey, ape, or other animal suitable for research on neurological disorders. In one embodiment, methods of the present invention are carried out using an experimental animal for which an animal model of one or more neurological diseases exists. In another embodiment, methods of the present invention are carried out using an experimental animal as part of developing an animal model of one or more neurological diseases. In yet another embodiment, methods of the present invention are carried out using an experimental animal in which the effects of exposure to a neurotoxic amino acid or neurotoxic derivative thereof associated with neurological disorders are measured by studies of brain chemistry, structure, or function. In one embodiment, a subject is a human. In another embodiment, a subject is a human suffering from one or more neurological disorders. In another embodiment, a subject is a human who is asymptomatic for one or more neurological disorders. In another embodiment, a subject is a human who has been identified as being at risk for developing a neurological disorder. In yet another embodiment a subject is a human who is known or suspected of having been exposed to at least one neurotoxic amino acid or neurotoxic derivative thereof associated with neurological disorders.

All publications, patents and other references cited herein are incorporated by reference in their entirety. In case of conflict, the present specification, including definitions, will control.

As used herein, the singular forms "a," "and," and "the" include plural referents unless the context clearly indicates otherwise.

Analysis of Neurotoxic Amino Acids in Samples

In accordance with one aspect of the present invention, immunoassays, antibodies, and kits are provided for detecting the presence of one or more forms of neurotoxic amino acid associated with neurological disorders, in particular BMAA.

In accordance with one aspect, immunoassays and kits are provided for detecting the presence of a neurotoxin in a subject by analyzing a tissue sample from a subject to detect the presence of one or more forms of neurotoxic amino acids, in particular BMAA, that may be indicative of the presence of a neurotoxin. In accordance with another aspect, immunoassays and kits are provided for detecting an environmental source of a neurotoxin by analyzing an environmental sample to detect the presence of one or more forms of neurotoxic amino acids, in particular BMAA, that may be indicative of the presence of a neurotoxin.

It is understood that neurotoxic amino acids in a sample, in particular BMAA, can be present in a "free" form (e.g., cytosolic, circulating, unbound, easily released), "protein-bound" forms (e.g., bound to the surface of a protein or incorporated into the polypeptide chain of a protein), and both "free" and "protein-bound" forms may be associated with other cellular components (e.g., conjugated to sugars, lipids, or polymers (e.g., cellulose, chitin, amylose, proteoglycan), and may be modified, derivatized, or otherwise linked to other sample components (e.g., carbamate adduct). It is understood that any or all of these forms (e.g., free, protein-bound) may be detected by one of skill in the art, depending on the immunoassay used for detection. In one non-limiting exemplary embodiment, BMAA can exist in a tissue sample or an environmental sample in a free (unbound) form, or can exist in a protein-bound form, where the protein-bound form includes, but is not limited to, BMAA bound to the surface of a protein (e.g. by conjugation, covalent linkage, non-covalent linkage, as a side group, linkage via spacer groups, etc.) or BMAA incorporated into the amino acid chain forming the polypeptide backbone of a protein. In one embodiment, both free and protein-bound BMAA levels are determined. In one embodiment, only free BMAA levels are determined. In another embodiment, only levels of protein-bound BMAA are determined. In another embodiment, the total BMAA in a sample is determined after a sample is treated, e.g. by hydrolysis or digestion, such that all forms of BMAA present in the sample are released as "free" BMAA. In certain embodiments, one of skill in the art can determine one or more BMAA conjugates of interest in a sample, and can determine whether the immunoassay or antibody being used is suitable to detect the BMAA conjugate(s) and whether the sample is to be treated to make the BMAA conjugate(s) available for detection. In other embodiments, immunoassays are provided such that additional amino acids, proteins, or other components are determined in addition to BMAA.

It is understood that immunoassays, antibodies, and kits provided herein can be utilized by one of skill in the art to analyze any sample in accordance with the present invention, including but not limited to, tissue samples from a subject, and environmental samples used in environmental screening. It is understood that one of skill in the art can modify methods of the invention as necessary to accommodate specific features of a sample, e.g., as necessary to prepare a keratinous tissue sample for analysis, or to prepare an environmental sample that includes material having cellulose, chitin or proteoglycan cell walls.

Antibodies Against Neurotoxic Amino Acids and Neurotoxic Derivatives

The present invention provides antibodies that bind neurotoxic amino acids and neurotoxic derivatives thereof, and further provides methods and kits for utilizing these antibodies for detecting the presence of at least one neurotoxic amino acid or neurotoxic derivative thereof in a sample. In accordance with one aspect, the invention provides antibodies that bind BMAA, and methods and kits for utilizing these antibodies for detecting the presence of BMAA in a tissue sample. In accordance with one aspect, the invention provides methods and kits for utilizing these antibodies for detecting the presence of BMAA in an environmental sample. In accordance with another aspect, the invention provides immunoassay for determining BMAA in a tissue sample or an environmental sample.

As discussed above, the term "antibody" or "antibodies" as used herein, encompasses immunoglobulins, immunoglobulin fragments, intact antibodies, single chain antibodies, antibody fragments, sera reactive against an antigen (antisera raised against an antigen), naturally occurring antibodies (i.e., resulting from expression of endogenous genetic sequences), recombinant antibodies, humanized antibodies, chimeric antibodies, synthetic antibodies (synthesized antibodies), where an antibody can be, but is not limited to, a polyclonal antibody, a monoclonal antibody, an Fv (variable fragment), a single chain Fv (scFv), a Fab', or F(ab')2 fragment. It is understood that polyclonal antibodies may be prepared by immunizing a host animal with an antigen, recovering sera after immunization, and characterizing sera having binding specificity for the antigen (antisera against the antigen). It is understood that monoclonal antibodies may be prepared by recovering spleen cells from immunized animals and immortalizing the cells using methods known in the art, e.g. by fusion with myeloma cells, following by screening for clones expressing antibodies with desired specificity and affinity (Kohler and Milstein, 1975, *Nature* 256:495-497), and monoclonal antibodies can be further modified or optimized using recombinant DNA technology. It is understood that the term "antibody" or "antibodies" can refer in its original sense to a polypeptide substantially encoded by an immunoglobulin gene or fragments thereof, that specifically binds and recognizes an antigen target, e.g., as described at length in Paul, ed., *Fundamental Immunology* (3rd ed. 1993). The term "antibody" or "antibodies" includes antibody fragments such as fragments resulting from enzymatic or chemical cleavage of an intact antibody (polyclonal or monoclonal), or fragments that can be synthesized de novo, either by use of recombinant DNA methodology or by chemical synthesis, e.g., Fv or scFv. The term "antibody" or "antibodies" includes recombinant antibodies including chimeric antibodies, humanized antibodies, recombinant monoclonal antibodies, etc.

Smaller molecular weight compounds such as amino acids, certain drugs, organic compounds, metals, small toxins, as well as peptides and oligosaccharides having a molecular weight of less than 2-5 kDa, are not usually immunogenic even when administered in the presence of immune-system-stimulating adjuvant. In order to generate an immune response to these compounds, it is necessary to conjugate such compounds to an immunogenic carrier compound such as an immunogenic carrier protein. The term hapten is generally understood to refer to a smaller molecular weight compound conjugated to an immunogenic carrier compound, where it is understood that in the hapten-carrier configuration, the hapten can function as an antigen even when the smaller molecular weight compound may not be immunogenic by itself. A hapten-carrier conjugate is then used to immunize a recipient animal (e.g., mouse, rat, sheep, goat, or rabbit) according to well-known methods, to elicit an immune response in the recipient animal. Optional steps include mixing the hapten-carrier conjugate with an adjuvant (e.g., complete Freund's adjuvant, CFA) for the initial immunization, or multiple initial immunizations, and one or more "booster" immunizations. The products of the immune response are then collected and analyzed to identify antibodies reactive against the hapten.

Methods for generating antibodies using hapten-carrier conjugates are well known in the art. Protocols for selecting immunogenic carrier compounds and conjugating haptens to immunogenic carrier compounds are well known in the art, e.g., as described in Harlow and Lane, *Antibodies: A Laboratory Manual*, Cold Spring Harbor Laboratory (Cold Spring Harbor, N.Y., 1988) pp. 78-87. Immunogenic carrier compounds can include, but are not limited to, thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH). Immunogenic carrier compounds can be selected that presumably do not occur in the sample that will be analyzed to determine the presence of the hapten (e.g., the neurotoxic amino acid or derivative thereof). This allows the antiserum to be used without having to isolate the anti-hapten antibodies from the anti-carrier antibodies. For example, KLH, a respiratory protein found in mollusks, is often selected because its large size makes it highly immunogenic and the numerous lysine residues available for conjugation make it very useful as a carrier for haptens, while the phylogenic separation between mollusks and other taxa reduces the risk of cross-reactivity between antibodies against the KLH carrier protein and the naturally occurring proteins in samples being analyzed to determine the presence of a neurotoxic amino acid or derivative. In one embodiment, BMAA or a BMAA derivative is conjugated to a carrier protein selected on the basis that it presumable does not occur in the samples that will be analyzed to determine the presence of BMAA or a BMAA derivative. In one embodiment, the carrier protein is KLH. In one embodiment, the carrier protein is BSA.

Antibodies against small molecules such as amino acids and amino acid derivatives are known in the art. U.S. Pat. No. 4,762,781 describes making and using antibodies against a variety of small amine-containing molecules; U.S. Pat. No. 5,112,738 describes making and using antibodies against histamine; Gefford et al. (1985, *J Neurochem* 44:1221-1228) describes making and using antisera against indolealkylamines. U.S. Pat. No. 6,608,178 describes the preparation and use of antibodies specific for the serotonin metabolite 5-hydroxytryptophol (5-HTOL) to detect recent alcohol consumption, where antibodies were developed that were specific for 5-HTOL or a glucuronide or sulphate conjugate of 5-HTOL, and had no specific binding activity to other compounds such as serotonin (5-hydroxytryptamine, 5-HT), the serotonin metabolite 5-hydroxyindole-3-acetic acid (5-HIAA), and structurally related indoles and other glucuronides. Making and using polyclonal antibodies against excitatory amino acids such as glutamate have been described by numerous groups, e.g., Hepler et al. (1983, *J Histochem Cytochem* 36:13), Petrusz et al. (1990, *Brain Res* 529:339) and Ordronneau et al. (1991, *J Immunol Methods* 142:169-176).

Both polyclonal and monoclonal antibodies against various amino acids and amino acid derivatives such as neurotransmitters are known in the art and commercially available, e.g., polyclonal anti-aspartate, polyclonal anti-GABA, polyclonal anti-glutamate, polyclonal anti-serotonin; monoclonal anti-GABA, monoclonal anti-aspartate, and monoclonal anti-glutamate, all available from Sigma Aldrich Co., St. Louis, Mo., or polyclonal antibodies against amino acids available from Signature Immunologics (Salt Lake City Utah).

Without wishing to be bound by this theory, it should be noted that haptens based on single molecules coupled to carrier compounds nearly always present linear determinants, which are molecular configurations in space that are characterized by adjacent interaction sites with restricted mobilities. Linear determinants present a very restricted set of targets to the immune system, such that antibodies that bind hapten targets virtually always attack the same or overlapping linear epitopes to the extent that binding is mutually exclusive. Thus, anti-hapten antibodies produced by polyclonal methods very often have monoclonal properties as far as molecular selectivity is concerned. This is important for at least two reasons: (a) the limiting property of a specific anti-hapten antibody is typically its affinity for its hapten target; and (b) polyclonal techniques usually provide a faster and easier method for finding a high-affinity, selective anti-hapten antibody than monoclonal methods. Whereas the affinities of antibodies for nonlinear determinant immunogens such as large proteins are complex, this should be contrasted with the case of hapten immunogens with very small, linear antigenic determinants, where there is a convergence of virtually all useful antibodies on a very narrow range of affinities. Furthermore, although components of linear determinants may have some mobility, this motion is usually limited, such that a linear determinant might exist in a few configurations that present different targets, and antibodies may be generated against different target configurations.

As provided herein, a neurotoxic amino acid or neurotoxic derivative thereof is conjugated to an immunogenic carrier compound to form an immunogenic hapten-carrier conjugate that is administered to a recipient animal, an immune response is generated against the hapten-carrier conjugate, and the products of the immune response are then analyzed to identify antibodies reactive against the neurotoxic amino acid or neurotoxic amino acid derivative of interest. In one embodiment, BMAA is conjugated to an immunogenic carrier protein to form an immunogenic BMAA-carrier protein conjugate that is administered to a recipient animal, an immune response is generated against the BMAA-carrier protein conjugate, and the products of the immune response are then collected and analyzed to identify antibodies reactive against BMAA or the BMAA derivative. In one embodiment, BMAA is conjugated to KLH as the carrier protein to form a KLH-BMAA conjugate that is administered to a recipient animal, an immune response is generated against the KLH-BMAA conjugate, and the products of the immune response are then analyzed to identify antibodies reactive against BMAA or the BMAA derivative. In another embodiment, BMAA or a BMAA derivative is conjugated to BSA as the carrier protein to form a BSA-BMAA conjugate.

In accordance with one aspect of the invention as provided herein, antibodies raised against an immunogenic hapten-carrier conjugate are then tested against the hapten conjugated to a second carrier that is distinct from the carrier used in the immunogenic hapten-carrier conjugate. Further in accordance with this aspect, one of skill in the art can choose a second, distinct, carrier relying on the assumption that it is unlikely that the recipient animal would be immunoreactive against the second carrier, such that analysis of the products of the immune response against an immunogenic hapten-carrier conjugate can be performed in such a way that only the reactivity of antibodies that bind the hapten are detected. In non-limiting exemplary examples presented below, KLH-BMAA conjugates are used to generate an immune response in rabbits, i.e., antisera raised against KLH-BMAA conjugates. Antisera are collected after immunization, and the antisera raised against KLH-BMAA conjugates are then evaluated using BSA-BMAA conjugates to detect and characterize antibodies that bind BMAA. As demonstrated in non-limiting exemplary embodiments in the Examples below, BSA-BMAA conjugates can be used in immunoassays to test antisera raised against KLH-BMAA conjugates, e.g., BSA-BMAA conjugates are used to coat microtiter plates for antibody capture assays to test antisera for antibodies that react with BMAA. Without wishing to be bound by this theory, it is assumed that if KLH is not present during tests of the antisera, then any antibodies against the KLH portion of the immunogenic hapten-carrier conjugate will not be detected, even if antibodies against KLH are present. In accordance with a further aspect of the invention, and as presented in non-limiting exemplary embodiments in the Examples below, products of the immune response (e.g., antisera) against immunization with immunogenic KLH-BMAA conjugates can be immunoprecipitated with KLH to remove any anti-KLH antibodies present.

Conjugating the hapten to the immunogenic carrier compound depends on the type and number of reactive groups available on the hapten and the carrier. Conjugating the hapten to the immunogenic carrier compound may further include introducing a conjugating linker or spacer between the hapten and the carrier compound. Linkers and spacers may be selected by one of skill in the art according to various criteria including, but not limited to, minimizing changes to the structural conformation of the hapten during conjugation and subsequent presentation to the recipient animal immune system, and facilitating presentation of the hapten for recognition by antibodies in immunoassays. Linkers and spacers include, but are not limited to, glutaraldehyde (Glu or GLU) and carbodiimide (Edc or EDC) linkers. In various embodiments, glutaraldehyde can be used to couple amino groups to amino groups, MBS (m-maleimidobenzoic acid-N-hydroxysuccinimide) can be used to couple amino groups to sulfhydryl groups, and carbodiimide can be used to couple amino groups to carboxyl groups. (See, *Antibodies: A Laboratory Manual*, E. Harlow and D. Lane, eds., Cold Spring Harbor Laboratory (Cold Spring Harbor, N.Y., 1988).

In one embodiment, BMAA or a BMAA derivative is conjugated to KLH as the carrier protein using glutaraldehyde (GLU) to form a KLH-GLU-BMAA (KGB) conjugate that is administered to a recipient animal, an immune response is generated against the KGB conjugate, and the products of the immune response (antisera) are then analyzed to identify antibodies reactive with BMAA or the BMAA derivative. In one embodiment, BMAA or a BMAA derivative is conjugated to KLH as the carrier protein using carbodiimide (EDC) to form a KLH-EDC-BMAA (KEB) conjugate that is administered to a recipient animal, an immune response is generated against the KEB conjugate, and the products of the immune response (antisera) are then analyzed to identify antibodies reactive with BMAA.

In one embodiment, BMAA or a BMAA derivative is conjugated to BSA as the carrier protein using glutaraldehyde (GLU) to form a BSA-GLU-BMAA conjugate that is administered to a recipient animal, an immune response is generated against the BSA-GLU-BMAA conjugate, and the products of the immune response are then analyzed to identify antibodies reactive with BMAA or the BMAA derivative. In one embodiment, BMAA or a BMAA derivative is conjugated to BSA as the carrier protein using carbodiimide (EDC) to form a BSA-EDC-BMAA conjugate that is administered to a recipient animal, an immune response is generated against the BSA-EDC-BMAA conjugate, and the products of the immune response are then analyzed to identify antibodies reactive with BMAA or the BMAA derivative.

Non-limiting exemplary embodiments of conjugation, immunization, and characterization procedures are disclosed in Examples below. FIG. 1 presents the outline of a non-limiting exemplary embodiment in which BMAA or a BMAA derivative is conjugated to KLH as the carrier protein using GLU to form a KLH-GLU-BMAA (KGB) conjugate, or EDC to form a KLH-EDC-BMAA (KEB) conjugate, and each KLH-BMAA conjugate is administered to a recipient animal to generate an immune response against the KLH-BMAA conjugate. BMAA or a BMAA derivative is also conjugated to BSA as the carrier protein using GLU to form a BSA-GLU-BMAA (BGB) conjugate, or EDC to form a BSA-EDC-BMAA (BEB) conjugate, and the BSA-BMAA conjugates are used in analyzing the products of the immune response against the KLH-BMAA conjugates (antisera), to identify antibodies reactive with BMAA or the BMAA derivative.

In accordance with another aspect of the invention, antibodies raised against an immunogenic hapten-carrier conjugate prepared using a defined cross-linker (e.g., GLU or ECD) are then tested against the hapten conjugated to the same or a distinct carrier via a different cross-linker, as presented in non-limiting exemplary embodiments found in the Examples below.

Selectivity of Antibodies Against Neurotoxic Amino Acids and Neurotoxic Derivatives Antibodies reactive with neurotoxic amino acids and neurotoxic derivatives thereof must have an acceptably high affinity and specificity for the hapten target, combined with an acceptable level of selectivity. An acceptable level of selectivity includes binding to the hapten target, and having an acceptably low level of cross-reactivity with other antigens, in particular structurally similar antigens. Without wishing to be limited by this theory, because the physicochemical properties of the targets (epitopes) presented by haptens arise from a small number of nearly fixed residues, useful antibodies (even from polyclonal sources) often have a similar range of affinities for the hapten target, even when antibodies are polyclonal and even when antibodies from different sources are compared (e.g., antibodies produced in different source animals). The affinity of an antibody for a hapten of interest can be determined using methods known in the art, such as antibody capture assays using differing coating concentrations of hapten, or measurement of competitive inhibition of binding by adding increasing amounts of hapten to a sample for which a baseline level of binding has been determined. Likewise, the selectivity of an antibody for an antibody for a hapten of interest can be determined using methods known in the art, such as competitive assays in which other antigens are added to a sample for which a baseline level of binding to the hapten has been determined.

Cross-reactivity is sometimes seen when the products of the immune response, e.g. antisera or other antibody compositions, contain multiple antibodies targeting multiple similar antigens, often binding with different affinities and often targeting different epitopes. As noted above, hapten immunogens present very small, linear antigenic determinants, and anti-hapten antibodies generally attack the same or overlapping targets (linear epitopes) to the extent that binding is mutually exclusive and thus, anti-hapten antibodies produced by polyclonal methods very often have monoclonal properties as far as molecular selectivity is concerned Cross-reactivity is sometimes due to the property of a single antibody that a target or steric space that can be formed by more than one distinct molecule. As described above, selectivity for the hapten of interest, and cross-reactivity with other antigens, can be determined for a sample such as an antiserum or other antibody composition, using methods known in the art.

In accordance with one aspect of the invention, antiserum raised against a neurotoxic amino acid or derivative thereof is provided, wherein the antiserum shows an acceptably high affinity and specificity for the hapten target, combined with an acceptably low level of cross-reactivity with other antigens, such that the serum is used in methods and kits of the invention without extensive purification or enrichment. In accordance with one aspect, antiserum raised against BMAA-carrier protein conjugates (anti-BMAA antiserum) shows an acceptably high affinity and specificity for BMAA, combined with an acceptably low level of cross-reactivity with other antigens. In accordance with this aspect, antiserum raised against BMAA-carrier protein conjugates (anti-BMAA antiserum) substantially binds BMAA conjugates and free BMAA and does not substantially bind (i.e., does not bind in a significant amount, or does not bind in a detectable amount) to structurally similar amino acids. In accordance with this aspect, antiserum raised against BMAA-carrier protein conjugates (anti-BMAA antiserum) shows reactivity with BMAA conjugates and with free BMAA and does not substantially bind to, detectably bind to, or substantially cross-react with structurally similar amino acids, even when the structurally similar amino acids are present at relatively high concentrations. In non-limiting exemplary embodiments disclosed in the Examples below, antiserum raised against BMAA-carrier protein conjugates (anti-BMAA antiserum) shows reactivity with BMAA conjugates and with free BMAA and does not substantially cross-react with structurally similar amino acids including alanine, glutamine, tyrosine, glycyl-glycine, glycine, leucine, phenylalanine, gamma-aminobutyric acid (GABA), glutamic acid, and aspartic acid, even when the structurally similar amino acids are present at relatively high concentrations. In accordance with one aspect of the invention, the anti-BMAA antiserum provided herein can be used in immunoassays and kits of the invention without extensive purification or enrichment.

In accordance with another aspect, purification steps may be taken to remove undesirable material such as nonspecific antibodies or non-antibody proteins before the antiserum is used to determine the neurotoxic ammo acid or neurotoxic amino acid derivative of interest. In accordance with one aspect of the invention, a desired degree of specificity or purity can be achieved by enriching the products of an immune response such as antiserum raised against a neurotoxic amino acid or derivative thereof, using methods known in the art. Methods for purification and/or enrichment include, but are not limited to, use of Protein A/G chromatography, ammonium sulfate precipitation, and affinity chromatography. In one embodiment, antiserum raised against BMAA or a BMAA derivative conjugated to an immunogenic carrier protein is subjected to partial purification by ammonium sulfate precipitation. In non-limiting exemplary embodiments presented in the Examples below, antiserum raised against BMAA or a BMAA derivative conjugated to KLH is subjected to partial purification by immunoprecipitation with KLH to remove anti-KLH antibodies. In one embodiment, antiserum raised against BMAA or a BMAA derivative conjugated to an immunogenic carrier protein is subjected to affinity purification using an affinity column having BMAA or a BMAA derivative coupled to the column matrix.

Immunoassays, antibodies, and kits are provided for distinguishing isomers of the same compound, e.g., for distinguishing L and D forms of an amino acid, or for distinguishing a neurotoxic isomer from the non-neurotoxic isomer of the same compound or compounds. As demonstrated in non-limiting exemplary embodiments presented in the Examples below, antibodies are provided that can distinguish L-BMAA from D-BMAA.

Methods for making and using antibodies having high affinity for target haptens and low cross-reactivity for similar haptens are known in the art. For example, certain commercially available polyclonal antibodies from Signature Immunologics, Inc. (Salt Lake City Utah) have high target specificity and low cross-reactivity for the free (unbound) form of certain amino acids. In one embodiment, antibodies are provided that have acceptably high affinity for the target neurotoxic amino acid or neurotoxic amino acid derivative, and low cross-reactivity with other amino acids. In one embodiment, antibodies are provided that have acceptably high affinity for BMAA or a BMAA derivative, and low cross-reactivity with other amino acids.

In accordance with one aspect, antibodies are provided that are reactive with the free (unbound) form of a neurotoxic amino acid or neurotoxic amino acid derivative, or with the protein-bound form of a neurotoxic amino acid or neurotoxic amino acid derivative, or with both forms of a neurotoxic amino acid or neurotoxic amino acid derivative. In one embodiment, antisera are provided that include antibodies specific for the free form, and antibodies specific for protein-bound forms. In one embodiment, antibodies capable of recognizing both the free form and the protein-bound form are provided. It is understood that protein-bound forms of a neurotoxic amino acid or neurotoxic amino acid derivative include, but are not limited to, the protein-bound form of a neurotoxic amino acid or neurotoxic amino acid derivative incorporated into the protein, e.g., into the polypeptide chain(s), and/or the protein-bound form of a neurotoxic amino acid or neurotoxic amino acid derivative otherwise associated with the protein, e.g., attached to the protein by covalent or noncovalent linkages, or conjugated to the protein through a spacer or linker group.

It is understood that polyclonal antibodies, or a composition such as antiserum containing polyclonal antibodies, may include antibodies that recognize different epitopes. It is understood that antibodies may be provided that recognize the free (unbound) form of BMAA or a BMAA derivative, and that antibodies may be provided that recognize the protein-bound form(s) of BMAA or a BMAA derivative, and that antibodies may be provided that can recognize both the free (unbound) form and the protein-bound form(s) of BMAA or a BMAA derivative. It is understood that protein-bound forms of BMAA or a BMAA derivative include, but are not limited to, BMAA or a BMAA derivative incorporated into the protein, e.g., into the polypeptide chain(s), and/or BMAA or a BMAA derivative otherwise associated with the protein, e.g., attached to the protein by covalent or noncovalent linkages, or conjugated through a spacer or linker group. As presented in non-limiting exemplary embodiments in the Examples below, an anti-BMAA polyclonal antibody, or an antiserum containing antibodies raised against BMAA, may be reactive with free BMAA, with conjugated BMAA, and with protein-bound BMAA.

In embodiments in which monoclonal antibodies are provided, one of skill in the art can screen antibody-producing hosts or clones individually to identify those clones having the desired level of steric specificity for neurotoxic amino acids or neurotoxic amino acid derivatives.

If considered necessary, the affinity of an antibody for different haptens having similar steric configurations will be mapped, to determine the relative affinities for different targets and the affinity for neurotoxic amino acids or neurotoxic amino acid derivatives.

Immunoassays and Antibodies to Detect the Presence of Neurotoxic Amino Acids

Antibodies as provided herein can be used in immunoassays by one of skill in the art to detect the presence, level (amount), and location of neurotoxic amino acids and neurotoxic amino acid derivatives in samples such as tissue samples or environmental samples. Immunoassays of the present invention can be carried out to analyze free (e.g., unbound, unconjugated, cytosolic, circulating) forms of neurotoxic amino acids or neurotoxic derivatives thereof, protein-bound forms of neurotoxic amino acids or neurotoxic derivatives thereof, or conjugated forms of neurotoxic amino acids or neurotoxic derivatives thereof associated with neurological disorders (e.g., sugar conjugates, lipid conjugates, or carbamate adducts), where any or all of these forms may be analyzed. One of skill in the art can determine which forms of neurotoxic amino acid(s) or neurotoxic derivative(s) thereof are present in a sample, and which forms are of diagnostic or predictive interest for a given embodiment. Antibodies and immunoassays as provided herein may be used in conjunction with physico-chemical methods for determining the presence, levels, and location of neurotoxic amino acids and neurotoxic amino acid derivatives described elsewhere in the present disclosure.

Suitable immunoassays and immunoassay formats for use with the antibodies provided herein are well known in the art. Homogeneous immunoassay formats that do not require separation of the bound antibody-neurotoxic amino acid complex from the rest of the assay components, are suitable for determining the presence, levels, and location of neurotoxic amino acids and neurotoxic amino acid derivatives as provided herein. Heterogeneous immunoassay formats that require at least one separation step, often utilizing a solid phase reagent such as a magnetic particle or plastic bead, to remove the bound antibody-neurotoxic amino acid complex from the rest of the assay components, are suitable for determining the presence, levels, and location of neurotoxic amino acids and neurotoxic amino acid derivatives as provided herein. It is understood that one of skill in the art can select and adapt immunoassay formats as necessary. Suitable immunoassay formats include, but are not limited to, agglutination-based assays, precipitation-based assays ("Ouchterlony" assays), radioimmunoassays, fluoroimmunoassays, chromogenic or colorimetric immunoassays, heterogeneous enzyme immunoassays, heterogeneous fluorescent immunoassays, homogeneous immunoassays including techniques such as fluorescence quenching or enhancement, fluorescence polarization, enzyme substrate-labeled immunoassays, prosthetic group-labeled immunoassays, enzyme modulator-labeled immunoassays (e.g., using inhibitor labels), enzyme-labeled immunoassays, energy transfer immunoassays, chemically-excited fluorescence immunoassays, and double antibody steric hindrance immunoassays, or other immunoassays as described e.g., in Harlow and Lane, *Antibodies: A Laboratory Manual*; Cold Spring Harbor Laboratory: Cold Spring Harbor, N.Y., 1988.

Immunoassay formats for use in an immunoassay to detect neurotoxic amino acids and neurotoxic amino acid derivatives, in particular BMAA, include but are not limited to enzyme-linked immunosorbent assays (ELISA) using antibodies or antigens in an assayable detection system, where suitable ELISA formats may include antibody capture ELISA, competitive ELISA, or indirect competitive ELISA, as described e.g., in Crowther, 1995. "ELISA. Theory and Practice" *Methods Mol. Biol.* 42:1-223, Engvall and Perlmann, 1971, "Enzyme-linked immunosorbent assay (ELISA). Quantitative assay of immunoglobulin G" *Immunochem.* 8:871-874, Davies, 1994, "Principles" in, *The Immunoassay Handbook*. D. Wild, ed. Stockton Press, New York, p. 3-47, and Harlow and Lane, *Antibodies: A Laboratory Manual*; Cold Spring Harbor Laboratory: Cold Spring Harbor, N.Y., 1988, Appendix F, and in Chu et al. (1989, *Appl Environ Microbiol* 55:1928-1933) and Metcalf et al. (2000, *Water Research* 34:2761-2769). The term "enzyme immunoassay" (EIA) is also commonly used to refer this immunoassay format.

In accordance with one aspect, antibodies as provided herein are unlabelled antibodies that are used as "primary" antibodies in traditional immunoassay formats. Accordingly, antibodies as provided herein will be detected and measured by a detectable secondary antibody that recognizes the primary antibody. Methods for selecting and using detectable secondary antibodies are known in the art. Suitable detectable secondary antibodies can be coupled to an enzyme such as horseradish peroxidase (HRP), alkaline phosphatase, lysozyme, glucose-6-phosphate dehydrogenase and the like, where coupling can be accomplished by conventional techniques using various cross-linking agents such as glutaraldehyde, dimaleimide or thiol reagents as described by Freytag et al. (1984, *Clin. Chem.* 30:417-420), or may be coupled to biotin or avidin, or may be directly labelled, e.g., with a radioactive label. Detecting the amount of secondary antibody bound to primary antibody bound to a neurotoxic amino acid or a neurotoxic amino acid derivative, allows detection and quantitation of the components.

In accordance with another aspect, antibodies as provided herein may be directly labelled, e.g., radiolabelled antibodies, or antibodies labelled with fluorescent moieties (fluorophores), luminescent moieties, chemiluminescent moieties, colloidal gold, dye moieties, enzyme-coupled antibodies, biotin-labelled antibodies, avidin-labelled antibodies, streptavidin-labelled antibodies, or antibodies labelled with other detectable moieties, in accordance with protocols that are well-known in the art, for direct detection and quantitation of the binding of antibodies to neurotoxic amino acids or derivatives thereof. In a non-limiting exemplary embodiment, labelled anti-BMAA antibodies are provided, e.g., biotin-labelled anti-BMAA antibodies.

In accordance with one aspect, an antibody capture immunoassay is provided to determine the presence and affinity of antibodies as provided herein, i.e., antibodies reactive with a neurotoxic amino acid or a neurotoxic amino acid derivative. In this assay, known amounts of unlabelled neurotoxic amino acid or derivative are coupled to a solid support, e.g., by coating a series of wells of a multi-well microtiter plate with serial dilutions of a stock solution, such that each well contains a known amount of neurotoxic amino acid or derivative, and antibodies as provided herein ("primary antibodies) are added to assay wells and "captured" on the solid support by binding to neurotoxic amino acid or derivative coupled to the solid substrate, and detected by a detectable secondary antibody that recognizes the primary antibody. The amount of primary antibody bound to ("captured by") the neurotoxic amino acid or derivative bound to solid support in each assay is determined by measuring the amount of detectable secondary antibody bound to the primary antibody, by methods known in the art. In one embodiment, antiserum raised against a neurotoxic amino acid or a neurotoxic amino acid derivative are used in an antibody capture assay to detect the level of antibodies reactive with neurotoxic amino acid or a neurotoxic amino acid derivative that are present in the antiserum. In one embodiment, antiserum raised against BMAA or a BMAA derivative is used in the antibody capture assay and antibodies binding to BMAA or a BMAA derivative coupled to the solid support are measured.

In accordance with one aspect, an indirect competitive ELISA is provided to determine the ability of antibodies as provided herein to bind the free (unbound) form of the neurotoxic amino acid or neurotoxic amino acid derivative used to generate the antibodies. In this assay, known amounts of unlabelled neurotoxic amino acid or derivative are coupled to a solid support, e.g., by coating a series of wells of a multi-well microtiter plate with serial dilutions of a stock solution, such that each well contains a known amount of neurotoxic amino acid or derivative. Antibodies as provided herein are used as "primary" antibodies, and free neurotoxic amino acid or neurotoxic amino acid derivative are added to the assay wells, and antibody capture in the presence of known amounts of the free neurotoxic amino acid or neurotoxic amino acid derivative are compared with antibody capture in the absence of free neurotoxic amino acid or neurotoxic amino acid derivative. As disclosed in non-limiting exemplary embodiments presented in the Examples below, indirect competitive ELISA can be performed to determine the reactivity of antisera raised against BMAA conjugates with free BMAA, to establish that antibodies that bind to free BMAA are provided.

In accordance with one aspect, an immunoblot assay is provided to determine the ability of antibodies as provided herein to bind neurotoxic amino acids or neurotoxic amino acid derivatives in a sample. In accordance with one aspect, immunoblot assays can be performed using a "dot blot" format on a total cell extract or a protein preparation from the sample to determine whether antibodies as provided herein are reactive with any components present in the sample. In accordance with another aspect, immunoblot assays can be performed in a "Western blot" format wherein proteins in a protein-containing extract of a sample are separated, e.g., using SDS-PAGE to separate proteins on the basis of size and/or charge, after which the separated proteins are transferred to a membrane, e.g., nylon or nitrocellulose, and antibodies as provided herein as used in an immunoassay to detect protein-bound neurotoxic amino acids or neurotoxic amino acid derivatives on the membrane. In one embodiment, antibodies raised against BMAA (BMAA-KLH conjugates) as provided herein are used to detect BMAA or BMAA derivatives on a Western blot of a protein preparation from a tissue sample or an environmental sample.

In accordance with one aspect, protein extracts are prepared from tissue samples or environmental samples, and an immunoassay for BMAA or BMAA derivatives is performed on the protein extract as provided herein, where recognition of protein bands by antibodies is understood to indicate that the sample may contain protein-bound BMAA or BMAA derivatives. In one embodiment, a subject is screened for exposure to an environmental source of BMAA by obtaining a tissue sample from the subject, contacting the tissue sample with an antibody composition including at least one antibody that binds BMAA under conditions that allow binding of the antibody to BMAA, and detecting antibody bound to BMAA in the tissue sample, wherein antibody binding to the tissue sample indicates that the tissue contains BMAA, thus indicating that the subject has been exposed to an environmental source of BMAA.

In one embodiment, an environmental source of BMAA is detected by obtaining an environmental sample, contacting the environmental sample with an antibody composition including at least one antibody that binds BMAA under conditions that allow binding of the antibody to BMAA, and detecting antibody bound to BMAA in the environmental sample, wherein antibody binding to the environmental sample indicates that the environmental sample contains BMAA and thus is an environmental source of BMAA. In one embodiment, a cyanobacterial source of BMAA in an environmental sample is detected by contacting the environmental sample with an antibody composition including at least one antibody that binds BMAA under conditions that allow binding of the antibody to BMAA, detecting antibody bound to BMAA in the environmental sample, and comparing the antibody binding to the environmental sample with antibody binding to samples of cyanobacteria, and determining whether the antibody binding to the environmental sample indicates the presence of a cyanobacterial source of BMAA.

In one embodiment, an immunoblot ("Western blot") assay of a protein extract of a tissue sample is performed using an antibody composition including at least one antibody that binds BMAA (e.g., antiserum raised against BMAA), and protein bands recognized by antibodies are identified. In one embodiment, an immunoblot or "Western blot" assay of a protein extract of an environmental sample is performed using an antibody composition including at least one antibody that binds BMAA (e.g., antiserum raised against BMAA), and protein bands recognized by antibodies are identified. In one embodiment, an immunoblot or "Western blot" assay of a protein extract of a keratinous tissue sample is performed, and protein bands recognized by antibodies of the present invention are identified. In another embodiment, an immunoblot or "Western blot" assay of a protein extract of a neurological tissue sample is performed, and protein bands recognized by antibodies of the present invention are identified.

In accordance with one aspect, antibodies that are reactive with protein-bound BMAA are used for in situ labelling or imaging applications, e.g. in immunohistochemical applications wherein the antibodies bind to lesions containing protein-bound neurotoxic amino acids or neurotoxic amino acid derivatives. Protocols for immunocytochemistry to detect small molecules such as amino acids in histological specimens are known in the art, e.g., high performance immunocytochemistry on epoxy-embedded specimens using rabbit polyclonal antibodies from Signature Immunologics, Inc. (Salt Lake City Utah) and gold-conjugated or fluorophore conjugated anti-rabbit secondary antibodies, for example as described at http://www.immunologics.com/hpi.html.

Amplification can be used to enhance the strength and/or selectivity of the signal. One of skill in the art can likewise modify neurotoxic amino acids and neurotoxic amino acid derivatives to yield labelled conjugates detectable by the immunoassay of the present invention.

Immunoassay and antibodies as provided herein can be used by one of skill in the art to analyze samples for neurotoxic amino acids and neurotoxic derivatives thereof, where samples include but are not limited to, tissue samples and environmental samples. Immunoassays as provided herein can be used to analyze tissue samples obtained from a living subject (ex vivo, in vitro), tissue samples present in a living subject (in vivo), or preserved specimens such as stored tissue, biopsy and/or autopsy samples, or museum specimens. Stored tissue may be frozen tissue, histological specimens, tissue dried on solid storage media, or other forms of stored tissue.

Antibodies as provided herein can be used in vivo, in imaging and diagnostic applications to detect neurotoxic amino acids and neurotoxic derivatives thereof in a subject. In particular, antibodies as provided herein can be used for in vivo diagnostic imaging to detect neurotoxic amino acids or neurotoxic derivatives thereof in bodily fluids, or in a body lumen, or in other body tissues. In one embodiment, antibodies reactive with protein-bound BMAA are introduced into a body lumen such as the spinal cord, a blood vessel, a ureter, a urethra, an esophagus, a cervix, a uterus or a bladder, wherein antibodies can bind to proteins containing BMAA in bodily fluids in the lumen, or to proteins containing BMAA in tissues on the walls of the lumen. In another embodiment, antibodies reactive with protein-bound BMAA are introduced into a tissue or organ, e.g., by perfusion, wherein antibodies can bind to proteins containing BMAA in situ in the tissue or organ. Antibodies of the invention are given in a dose that is diagnostically effective to enable detection of protein-bound BMAA for a particular application. For in vivo imaging, the antibody may be labelled or otherwise coupled to a detectable marker so that the antibody can be directly detected. In another embodiment, a detector such as a secondary antibody is introduced into the body lumen and detects the antibody bound to BMAA. Detectable markers that can be coupled to antibodies of the invention include radioisotopes such as $^{131}$I, $^{125}$I, $^{123}$I, $^{18}$F, $^{19}$F, $^{11}$C, $^{13}$C, $^{14}$C, $^{75}$Br, $^{76}$Br, or $^{3}$H. Markers may be paramagnetic compounds, e.g., compounds including lanthanides. Markers may be contrast agents suitable for detection by contrast-enhanced ultrasound, e.g., microbubbles having a suitable biocompatible shell and a core of heavy gas (perfluorocarbon or nitrogen) conjugated to the antibody. For in vivo diagnostic imaging, the type of detection instrument to be used is a major factor in selecting the detectable marker, such that markers may be selected for X-ray (e.g., $^{125}$I, $^{57}$Co, Technetium-99m ($^{99m}$Tc)), ultrasound (e.g., perflutren microbubble), MRI (e.g., gadolinium, $^{19}$F, $^{1}$H), PET ($^{18}$F), computer assisted tomography (CAT), magnetic resonance spectroscopy (MRS), single-photo emission computed tomography (SPECT, bioluminescence image (BLI) or other applications. In some embodiments, the labelled antibody bound to BMAA is detected or measured locally in an organ or tissue. In some embodiments, the labelled antibody bound to BMAA is measured systemically, by scanning all or a portion of the subject using imaging methods such as X-ray, ultrasound, PET, or MRI. Pharmaceutical compositions suitable for administration for in vivo imaging and diagnostic applications are provided, wherein the pharmaceutical compositions include antibodies reactive with protein-bound BMAA and a detectable marker that allows detection of the antibody bound to BMAA. Protocols for introducing and detecting markers such as antibodies to detect lesions are found in U.S. Pat. Nos. 5,716,595; 6,375,925; and 6,782,289, herein incorporated by reference.

Sample Preparation

It is understood that immunoassays, antibodies, and kits of the present invention may include preparation steps to accommodate specific features of a sample, e.g., steps to prepare a tissue sample for analysis, or to prepare a subject for in vivo measurement/imaging, or to prepare an environmental sample for analysis. Sample preparation may include, but is not limited to, mechanical or chemical disruption of the sample, where chemical disruption includes but is not limited to hydrolysis (e.g., acid hydrolysis), enzymatic digestion, or solvent extraction (solvent partitioning), to release BMAA from the sample for detection by immunoassays and antibodies as provided herein.

In one embodiment, a keratinous tissue such as hair is hydrolyzed using strong acid and heating and an immunoassay for BMAA is performed on the neutralized hydrolysate. In another embodiment, hair is enzymatically digested using a protease mixture containing reductants and detergents, e.g., as described in U.S. Pat. No. 6,949,344, and an immunoassay for BMAA is performed on the digest. In another embodiment, neurological tissue such as brain tissue is first homogenized under acidic conditions (e.g., 0.1N trichloroacetic acid) and centrifuged to release free amino acids and precipitate proteins, then the pellet is subjected to hydrolysis using strong acid and heat (e.g., 6N HCl at 110° C. for 24 hours), after which an immunoassay of the neutralized supernatant is carried out to determine free BMAA in the sample and an immunoassay of the neutralized pellet hydrolysate is carried out to determine the protein-bound BMAA that was released from the pellet by hydrolysis.

In one embodiment, an environmental sample including cellulose is treated with cellulase to release cell contents and cell wall material for determination of BMAA. In one embodiment, an environmental sample including chitin is treated with chitinase to release cell contents and cell wall material for determination of BMAA.

In one embodiment, a sample may be treated to yield a plurality of sample fractions, and immunoassays of the present invention are used to determine BMAA in one or more of the resulting sample fractions. In one embodiment, a sample can be treated to yield a protein fraction and a soluble fraction, e.g. as disclosed in U.S. Pat. No. 7,256,002, wherein cyanobacteria, cycad seed tissue, flying fox (bat) hair and skin, and human brain tissue samples were treated to remove free amino acids (from a soluble or cytosolic fraction) and yield a protein fraction assumed to contain protein-bound BMAA, after which the protein fraction was hydrolyzed and BMAA in the hydrolysate was determined using HPLC. In another embodiment, a sample may be extracted with solvents of different polarities, e.g. to yield aqueous and lipophilic fractions.

In accordance with one aspect, the sensitivity of the BMAA immunoassay may be enhanced by sample concentration and/or sample clean-up prior to the immunoassay, in order to increase the BMAA concentration in a sample to a level amenable to current immunoassay procedures, and to remove potentially interfering substances. In a non-limiting exemplary embodiment, commercially available solid phase extraction (SPE) sorbents were assessed for their ability to retain BMAA from solution, and to then release BMAA in an elution step. Based on results from initial SPE screening, further testing of different polymeric SPE phases indicated that strong cation-exchange polymeric SPE sorbents (e.g., StrataXC) appeared to have acceptable BMAA retention and elution properties. In one embodiment, a sample is subjected to preliminary clean-up using SPE sorbents prior to immunoassay of the sample as provided herein. In one embodiment, a plurality of SPE phases is used in a multiphasic approach for retention and clean-up of BMAA from samples using serial SPE extraction of the sample prior to immunoassay as provided herein.

Screening for Neurological Disorders

The present invention provides immunoassays, antibodies, and kits for screening subjects having or at risk of having neurological disorders, by screening at least one tissue sample from the subject to detect the presence of BMAA. As provided herein, neurological disorders (also known as neurologic disorders, or neurologic diseases, or neurological diseases) are disorders that involve the central nervous system (brain, brainstem and cerebellum), the peripheral nervous (including cranial nerves), and the autonomic nervous system (parts of which are located in both central and peripheral nervous system). It is understood that neurological disorders may have complex etiologies, such that one or more environmental or genetic factors may contribute to development of a neurological disorder in a subject. Neurological disorders include well-characterized disorders or syndromes such as Alzheimer's disease, amylotropic lateral sclerosis (ALS), or Parkinson's disease, or may be signs (e.g., aphasia) or symptoms (e.g., tremors) that are observed in multiple disorders. It is further understood that the development of a neurological disorder in a subject may be due to one factor or a combination of factors. Likewise, it is understood that a particular neurological disorder in a subject may be due to different factors or different combinations of factors that resulted in the same neurological disorder in other subjects. Immunoassays as provided herein are suitable for use in screening for neurological disorders wherein one or more environmental or genetic factors may play a part.

Screening methods include but are not limited to, methods for diagnosing one or more neurological disorders in a subject, methods for confirming a diagnosis of one or more neurological disorders in a subject, methods for predicting the risk or likelihood of developing one or more neurological disorders in a subject, methods for predicting the severity of a neurological disorder in a subject, and methods for determining exposure of a subject to neurotoxic amino acids or neurotoxic derivatives thereof associated with developing neurological disorders. Methods of the present invention include methods for carrying out repeated testing to generate time series data on the presence and levels of neurotoxic amino acids or neurotoxic derivatives thereof in a subject, and/or the presence and levels of neurotoxic amino acids or neurotoxic derivatives thereof in environmental samples. Methods include correlating the presence or absence of a neurotoxic amino acid or neurotoxic derivative thereof in tissue samples from a subject, with other physical or psychological determinations relevant to assessing neurological disorders. Methods further include correlating the levels of a neurotoxic amino acid or neurotoxic derivative thereof measured in one or more tissue samples from a subject, with other physical or psychological determinations relevant to assessing neurological disorders. In one embodiment, tissue samples are obtained from a subject diagnosed as having a neurological disorder, BMAA levels are determined, and these results are compared with other physical or psychological measurements of the subject, as part of a method for diagnosing one or more neurological disorders.

Screening using immunoassays, antibodies, and kits of the present invention can be practiced to refine or confirm a diagnosis of one or more neurological disorders, to evaluate the risk of having or developing one or more neurological disorders, or to exclude other possible diagnoses. In one embodiment, immunoassays of the present invention are performed to detect the presence of BMAA in tissue samples from a subject who is currently asymptomatic for one or more neurological disorders. In another embodiment, immunoassays of the present invention are performed to detect BMAA levels in tissue samples from a subject who is currently symptomatic for one or more neurological disorders. In another embodiment, immunoassays of the present invention are performed to detect the presence of BMAA in tissue samples from a subject suspected of having a neurological disorder, and these results are compared with other physical or psychological measurements of the subject, as part of a method for diagnosing one or more neurological disorders. In a further embodiment, immunoassays of the present invention are repeatedly performed to measure BMAA levels in tissue samples over time, to identify subjects who may be at risk of developing a neurological disorder and may be in need of additional monitoring. In a further embodiment, immunoassays of the present invention are performed to detect the presence of BMAA in one or more tissue samples, and one of skill in the art can correlate BMAA levels with other measurements such as physical or psychological determinations relevant to assessing neurological disorders, and/or with genetic analysis of the subject (e.g., family history and/or genotyping tissue samples) to determine the risk or likelihood of having or developing a neurological disease.

In accordance with another aspect, methods are provided for longitudinal studies of neurological disorders by taking tissue samples at repeated intervals over a period of time and performing immunoassays to detect the presence of BMAA in each tissue sample, providing time series data on BMAA levels useful for longitudinal studies. In yet another embodiment, immunoassays of the present invention are repeatedly performed to detect the presence of BMAA in tissue samples from a subject over a period of time, where the level or amount of BMAA in each sample provides data on BMAA accumulation in tissues over time, which is useful for predicting the likelihood and/or timing and/or severity of future onset of one or more neurological disorders. In yet another embodiment, immunoassays of the present invention are repeatedly performed to detect the presence of BMAA in tissue samples from a subject over a period of time, where the level or amount of BMAA in each sample provides data on BMAA release from tissues over time, which is useful for predicting the likelihood and/or timing and/or severity of future onset of one or more neurological disorders.

The invention provides immunoassays, antibodies, and kits for use in screening for neurological disorders including but not limited to, Parkinson's disease (PD), Alzheimer's disease (AD), progressive supranuclear palsy (PSP), amyotrophic lateral sclerosis (ALS), and the neuropathological disease known as ALS-PDC (also known as ALS-PDC of Guam, or lytico-bodig disease). The teachings of the present disclosure provide sufficient guidance to identify other neurological disorders for which the present invention provides screening methods, where one of skill in the art can practice the methods of the present invention to detect the presence and determine the levels of BMAA in tissue samples from a subject, then compare these levels with other indicia of neurological disease in the subject, and ascertain whether a correlation exists between levels of BMAA in the sample and indicia of a particular neurological disease. Because distinct disorders often share similar signs and symptoms (e.g., tremors, dementia, aphasia), immunoassays, antibodies, and kits of the present invention may be suitable for use as part of an initial screening for neurological disease, wherein the results of the immunoassay-based initial screening are relied upon for determining what further tests are needed for a thorough assessment. For example, subjects with ALS-PDC can have symptoms similar to Alzheimer's disease or Parkinson's disease, or both diseases, and although ALS-PDC is considered a separate disorder, it is also possible for a subject with ALS-PDC to also suffer from Alzheimer's disease or Parkinson's disease. Likewise, subjects with Alzheimer's disease and subjects with other forms of dementia may have some similar symptoms, but may differ in the BMAA content of various tissues. Accordingly, measurement of BMAA levels in a subject may aid in identifying which neurological disorders are present are contributing to the signs and symptoms observed in the subject.

In accordance with one aspect, immunoassays of the invention can be performed using any tissue sample from a subject. In one embodiment, a tissue sample is analyzed to detect the presence of BMAA. In another embodiment, detecting the presence of BMAA includes determining the amount of BMAA present in the tissue sample. In another embodiment, a tissue sample may be analyzed to detect not only the presence of BMAA, but also the location of BMAA in the tissue in vivo or ex vivo. In another embodiment, a tissue sample is treated to yield at least two sample fractions and at least one fraction is analyzed to detect the present of BMAA. Levels (amounts) of free BMAA and/or protein-bound BMAA may be determined (quantified), according to the nature of the tissue sample and the question to be answered in a particular embodiment. In some embodiments, it may be desirable to determine both free and protein-bound BMAA levels. In other embodiments, it may be desirable to determine only free BMAA levels. In other embodiments, it may be desirable to determine only protein-bound BMAA levels. In some embodiments, the tissue may be completely chemically disrupted (e.g., by hydrolysis) such both free and protein-bound BMAA are collected in a single sample fraction (hydrolysate) that is analyzed to determine the total BMAA level in the sample.

Tissue samples may be obtained from a living subject, may be present in a living subject, or may be obtained from a preserved specimen such as stored tissue, biopsy and/or autopsy samples, or museum specimens. Stored tissue may be frozen tissue, histological specimens, tissue dried on solid storage media, or other forms of stored tissue. Suitable tissue samples include but are not limited to neurological tissue or non-neurological tissue. Neurological tissue can be associated with the central nervous system (CNS), including brain tissue or cerebral-spinal fluid (CSF), or may be associated with the peripheral nervous system (PNS). Neurological tissue can include tissue present in a living subject, including but not limited to cerebral-spinal fluid (CSF) suitable for in vivo imaging and diagnostics. Non-neurological tissue can be keratinous tissue, or non-keratinous tissue including but not limited to, blood, serum, lymph, saliva, or urine. Non-neurological tissue can be analyzed ex vivo or in vivo. For example, ex vivo analysis of blood can involve removing blood from a subject and analyzing the blood sample, while in vivo analysis of blood can involve detecting and imaging of blood in a body lumen such as a blood vessel.

Keratinous tissue includes, but is not limited to, hair, skin, nail, including fingernail or toenail, feather, claw, hoof, or horn. In accordance with one aspect of the invention, samples of keratinous tissue from a subject collected at multiple time points, e.g., hair or skin samples, can be analyzed to detect the present of BMAA and, if desired, to determine BMAA levels. In one embodiment, hair is analyzed to detect the presence of BMAA. In one embodiment, hair is analyzed to detect the total level (amount) of BMAA in the sample. In one embodiment, hair is analyzed to detect free BMAA and protein-bound BMAA separately (e.g. in separate sample fractions), where the levels (amount) of free BMAA and protein-bound BMAA may also be determined. In another embodiment, hair is analyzed to detect only free BMAA. In another embodiment, hair is analyzed to detect only protein-bound BMAA. In another embodiment, skin is analyzed to detect BMAA. In one embodiment, skin is analyzed to detect the total level (amount) of BMAA in the sample. In one embodiment, skin is analyzed to detect free BMAA and protein-bound BMAA separately (e.g. in separate sample fractions), where the levels of free BMAA and protein-bound BMAA may also be determined. In another embodiment, skin is analyzed to detect only free BMAA levels. In another embodiment, skin is analyzed to detect only protein-bound BMAA levels.

In another embodiment brain tissue is analyzed to detect the presence of BMAA, where brain tissue may be analyzed to determine BMAA levels in the tissue. In another embodiment, samples of cerebrospinal fluid (CSF) are analyzed in vivo or ex vivo to detect the presence of BMAA, where CSF may be analyzed to determine BMAA levels in the fluid. Brain or CSF tissue may be analyzed to determine the levels of protein-bound BMAA, free BMAA, or both protein-bound and free BMAA, wherein protein-bound BMAA may be bound to neuroproteins or to other proteins.

Screening for Environmental Factors Associated with Neurological Disorders.

In accordance with one aspect, immunoassays, antibodies, and kits are provided for screening for environmental factors associated with neurological disorders by detecting the presence of BMAA in environmental samples. Screening as provided herein includes, but is not limited to, testing environmental samples to determine actual or potential exposure of a subject to a neurotoxic amino acid or neurotoxic derivative thereof associated with neurological disorders. An environmental sample may be obtained from material that is ingested, e.g. a water sample or a food sample. An environmental sample may be material that is deliberately ingested, e.g., water used for drinking, or plants or animals that are part of the food supply or food chain. Alternately, an environmental sample may be obtained from material that is incidentally ingested, e.g., material from an organism whose contents or secretions become associated with other ingested material, such as cyanobacterial symbionts present in plants used for food, or cyanobacteria in water used for washing or drinking.

In one embodiment, immunoassays, antibodies, and kits of the present invention are provided to determine (quantitate) BMAA levels in environmental samples, to determine the actual or potential exposure of a subject to BMAA. Measurements of BMAA levels in environmental samples leads to a determination of potential or actual exposure to BMAA, and these measurements can be used to predict the likelihood that neurological disorders will develop in a subject exposed to these environmental samples. As disclosed in U.S. Pat. No. 7,256,002, HPLC analysis of samples from an archive of cyanobacteria showed that nearly all the strains that were tested produced BMAA. Further as disclosed in U.S. Pat. No. 7,256,002, the BMAA found in cycad tissues appears to be produced by cyanobacterial symbionts taken up by the cycads, such that other organisms that feed on cycads, such as human and "flying foxes" (bats), appear to ingest BMAA of cyanobacterial origin.

In accordance with another aspect, an environmental sample is water known to contain cyanobacteria. In another embodiment, an environmental sample is water suspected of containing cyanobacteria. In another embodiment, an environmental sample is water whose contents are unknown. In another embodiment, an environmental sample may be a food animal that ingests cyanobacteria-containing water, e.g., a fish, bird, deer, or domesticated animal. In another embodiment, an environmental sample may be lichen or moss or liverworts that contain or live in symbiosis with cyanobacteria.

In another embodiment, an environmental sample may be a marine or freshwater alga or a marine or freshwater fungus that contain or live in symbiosis with cyanobacteria. In another embodiment, an environmental sample may be a marine or freshwater invertebrate that contains or lives in symbiosis with cyanobacteria. In another embodiment, an environmental sample may be a stromatolite, or a petrochemical deposit, or a mineral deposit left by cyanobacteria. In another embodiment, an environmental sample may be a food animal that ingests a plant, lichen, moss, alga, marine invertebrate, that contain cyanobacteria or a stromatolite, petrochemical deposit, or mineral deposit left by cyanobacteria, e.g. a reindeer, caribou, deer, moose, marine or freshwater fish, bird, reptile, or domesticated animal.

In accordance with another aspect, an environmental sample is screened to determine if the sample is associated with a neurological disorder, by detecting the presence of cyanobacteria that produce a neurotoxic amino acid, in particular BMAA, in the environmental sample. Immunoassays, antibodies, and kits of the invention are performed to detect the presence of cyanobacteria of genera including, but not limited to, *Nostoc* and *Anabena*. By screening environmental samples to detect cyanobacteria that produce BMAA, it is possible to determine actual or potential exposure of a subject to environmental factors associated with a neurological disorder.

In accordance with another aspect, a plurality of environmental samples is tested to determine the presence and levels of neurotoxic amino acids associated with neurological disorders, in particular BMAA, at different levels throughout a food chain. Without wishing to be limited by this theory, biomagnification of factors associated with neurological disorders, e.g., BMAA, can occur by accumulation of a factor in tissues of organisms at different trophic levels, with the result that consumption of an organism from a higher trophic level may give a much higher exposure to a neurotoxin than consumption of an organism from a lower trophic level. In one exemplary embodiment, a plurality of environmental samples is tested in a food chain, including cycad coralloid roots, cycad leaves, cycad seeds, and tissue samples from flying foxes (bats) known to eat cycad seeds. In another embodiment, a plurality of environmental samples is tested in a food chain, including water, aquatic plants, food animals that ingest the water or aquatic plants, e.g., fish birds, a wild or domesticated animal, and carnivores that ingest plant-eating animals. In one embodiment, a plurality of environmental samples can be tested to determine whether a factor such as BMAA is found in a particular food chain. After testing a plurality of environmental samples, levels of a neurotoxic amino acid, e.g. BMAA, can be compared and analyzed for evidence of accumulation or biomagnification in the food chain.

In accordance with a further aspect, a tissue sample from a subject is also analyzed, in addition to testing environmental samples for a neurotoxic amino acid associated with neurological diseases. Screening at least one tissue sample from a subject provides data useful for determining accumulation or biomagnification of environmental factors (neurotoxic amino acids, in particular BMAA) in a food chain, and correlating levels of these environmental factors (e.g., BMAA) in each step of the food chain with the frequency or severity of neurological disorders in subjects that consume material from various trophic levels of the food chain. In one embodiment, a tissue sample from a subject with symptoms of, or a diagnosis of, a neurological disorder is analyzed to detect a neurotoxic amino acid associated with neurological diseases, in particular BMAA. In another embodiment, a tissue sample from a subject asymptomatic for a neurological disorder is analyzed to detect a neurotoxic amino acid associated with neurological diseases, in particular BMAA. This aspect of the present invention provides a powerful tool for linking neurological disorders with exposure to environmental factors that are known or suspected to be associated with neurological disorders.

In a non-limiting exemplary embodiment, U.S. Pat. No. 7,256,002 disclosed that elevated BMAA levels were detected in brain tissues of subjects who died of ALS-PDC after known exposure to food sources that were known or suspected to contain BMAA—i.e., the subjects who died of ALS-PDC were Chamorros who had eaten a traditional Chamorro diet at some time in their life, which likely included cycad flour and may have included flying foxes (bats), where measurements of BMAA levels in specimens of flying foxes showed high concentrations of BMAA, leading to the prediction that consumption of a single flying fox would have resulted in a dose of BMAA equivalent to the dose obtained by eating 174-1,014 kg of processed cycad flour. In addition, elevated BMAA levels were detected in one Chamorro subject who was asymptomatic for ALS-PDC and died of other causes, congruent with findings of neurofibrillary tangles in brain tissue of both affected (ALS-PDC) and unaffected (asymptomatic) Chamorros. In contrast, another Chamorro subject who was asymptomatic for ALS-PDC and died of other causes, did not have detectable BMAA levels in brain tissue.

Another aspect of the invention provides methods for detecting environmental contamination by environmental factors associated with neurological disorders. In a non-limiting exemplary embodiment, U.S. Pat. No. 7,256,002 disclosed that elevated BMAA levels were found in brain tissue of non-Chamorro (Canadian) subjects who had suffered from Alzheimers disease and in a non-Chamorro (Canadian) suffering from progressive supranuclear palsy (PSP), indicating that these subjects had been exposed to environmental sources of BMAA at some time in their life. In accordance with another aspect, bioaccumulation of cyanobacterial BMAA may occur through food chains, resulting in accumulation in tissues of subjects. Since the frequency of illness in a population exposed to neurotoxins is a function of dose, even low levels of progressive neurological disorders might be related to exposure to low concentrations of BMAA in water supplies contaminated by cyanobacteria. Accordingly, environmental screening as provided herein can be carried out to investigate possible environmental sources of BMAA or other environmental factors associated with neurological disorders. Environmental screening as provided herein can be carried out to prevent or minimize exposure of other subjects to BMAA or other environmental factors associated with neurological disorders, thereby decreasing the risk of developing a neurological disorder associated with BMAA or other factors.

In accordance with a further aspect, immunoassays, antibodies, and kits of the invention can be used to protect a subject from exposure to environmental factors associated with neurological disorders, by screening environmental samples prior to ingestion by the subject. In one embodiment, immunoassays, antibodies, and kits are provided to test food samples, including plant or animal matter, for BMAA. In another embodiment, immunoassays, antibodies, and kits are provided to test water supplies for BMAA. Kits for environmental screening for BMAA include materials for practicing methods of the invention to test water supplies, food supplies, and other environmental samples, to protect subjects from exposure to BMAA. In accordance with another aspect, immunoassays, antibodies, and kits of the invention can be used for public health purposes, e.g., to indicate contamination of a water supply or food source with cyanobacteria that produce BMAA.

Kits for Screening for Neurotoxic Amino Acids

The present invention provides kits comprising means for performing immunoassays of the present invention. In one embodiment, the present invention provides a kit for screening a subject having or at risk of having a neurological disorder, wherein the kit includes an immunoassay for determining the presence of BMAA in a tissue sample from the subject. In another embodiment, the present invention provides a kit for screening environmental samples for environmental factors associated with neurological disorders by determining the presence of BMAA in the sample, wherein the kit includes an immunoassay for determining the presence of BMAA in an environmental sample. Kits of the invention may include means for analyzing a plurality of types of samples, e.g. kits may include means for analyzing tissue samples from a subject as well as environmental samples such as water or food samples. Alternately, kits of the invention may only include means for analyzing one or a few types of samples, e.g. a kit may only include means for analyzing keratinous tissue samples such as hair.

Such a kit may comprise a carrier means compartmentalized to receive one or more container means such as vials, tubes, and the like, each of the container means comprising one of the separate elements to be used in the method. For example, one of the container means may comprise an antibody that binds BMAA, where the constituents may be present in liquid or lyophilized form, as desired. The kit may include additional container means comprising separate elements for detecting antibody binding to BMAA. If the antibody that binds BMAA is detectably labelled, then the kit may include one or more additional container means comprising reagents necessary to detect labelled antibody bound to BMAA, as well as any container means required to carry out detection reactions. For example, if the antibody that binds BMAA is labelled with biotin, a container means may comprise avidin or streptavidin reporter molecules, and reagents for allowing biotin-avidin or biotin-streptavidin to occur, while another container means may comprise reagents for removing unbound antibody and reporter molecules. If the antibody that binds BMAA is not detectably labelled, a kit may include additional container means comprising separate elements for detecting antibody binding to BMAA using a detectably labelled secondary antibody, including the reagents necessary to detect secondary antibody binding to the antibody that binds BMAA. For example, the kit may include an addition container means comprising a second antibody labelled with horseradish peroxidase (HRP), in liquid or lyophilized form, as desired. Another container means comprises reagents for incubating the secondary antibody with the sample and the antibody that binds BMAA, while another container means comprises reagents for removing unbound antibodies after incubation. Another container means comprises reagents for detecting HRP activity, e.g., HRP substrate. If necessary, an additional container means comprising means for visualizing HRP product. Depending on the immunoassay format, the sample may be planed into the container means for a particular step, or the contents of the container may be removed for use.

Preferably, kits of the invention include all components and reagents necessary to carry out an immunoassay as provided herein, e.g., vessels for manipulating samples and for carrying out reactions, and reagents for inducing an observable or otherwise measurable reaction to determine BMAA in the sample. Thus, kits may comprise a carrier means compartmentalized to receiver container means comprising all the elements provided with the kits.

Kits of the invention may also include "control" antibodies, e.g. null serum or an antibody that do not bind BMAA. Kits of the invention may include a "positive control" sample known to contain BMAA. Kits of the invention may include a "negative control" sample that is known to not contain BMAA. Kits of the invention may include a panel of "control" or "standard" samples of a known amount of BMAA whereby a standard curve may be constructed for purposes of quantitation and calibration. Kits may include means for analyzing a plurality of samples, and may include means for performing immunoassays at repeated intervals that may stretch over days, months, or years, e.g., for use in longitudinal studies as described above.

Kits may further include means for collecting samples. Means for collecting a tissue sample from a subject are known in the art, e.g. scissors or clippers to obtain a hair or nail sample, or a device for obtaining a skin sample such as a plastic stick or buccal swab, or a device for obtaining a fluid sample such as a lancet to produce a blood sample or a hollow needle to withdraw CSF. Means for collecting environmental samples are also known in the art, e.g., sealable vessels for collecting liquid samples. Means for collecting samples may further include means for storing samples, e.g. a vessel (container) or a solid substrate solid supports, multititer plates, test tubes, trays and the like, where storage means may further include reagents to stabilize and/or preserve the sample.

Kits of the invention may include means for sample preparation as described elsewhere. The kit may contain means for preparing the tissue sample for analysis, such as means for mechanically disrupting the tissue sample or means for chemically disrupting the tissue sample using, e.g., strong acid, enzyme, detergents, and the like, as described elsewhere in the disclosure. Means for sample preparation may include means for treating a sample to yield different fractions, thereby providing means for separately analyzing protein-bound BMAA (e.g. in a protein fraction) and free BMAA (e.g. in a soluble or cytosolic fraction) in the sample. Means for sample preparation may include means for total sample extraction, and may include means for analyzing both protein-bound BMAA and free BMAA in the total sample extract. It is understood that one of skill in the art can prepare a kit suitable for use in any particular immunoassay, the precise physical embodiment of which will depend upon the type of assay contemplated.

A preferred kit is a mercantile unit prepared for determining the presence of BMAA in a tissue sample from a subject. Another preferred kit is a mercantile unit for determining the presence of BMAA in an environmental sample. The components of such a kit may include, for example, various diluents and buffers in addition to the antibody or antibodies, microtiter plates, standards, reagents and the like, as described previously. This kit may also contain a neurotoxic amino acid conjugate bound to a solid support, or an antibody bound to a solid support. The solid support may be a surface such as a microtiter plate, or a material that allows a sample applied to the material to diffuse or be transported along one or more of its dimensions, such as a "dipstick." or a permeable material wherein neurotoxic amino acids and neurotoxic derivatives thereof bind to antibodies and form detectable complexes while unbound material pass through, such as beads in a column. This kit may also contain a labeled antibody or a labeled conjugate of one or more neurotoxic amino acids and neurotoxic derivatives thereof being analyzed.

In accordance with one aspect, a kit includes one or more compositions for use in practicing at least one method of the invention, packaged into suitable packaging material. In accordance with one aspect, a kit of the present invention includes a label and/or a packaging insert for practicing at least one method of the invention. As used herein, the term "packaging material" refers to a physical structure housing the components of the kit. The packaging material can maintain the components in a sterile and/or stable condition, and can be made of material commonly used for such purposes (e.g., paper, corrugated fiber, glass, plastic, foil, ampules, etc.). The terms "label" and "packaging insert" refer to appropriate instructions for practicing at least one method of the invention. It is understood that the instructions may be written instructions in one or more languages, schematic instructions represented by drawings, photos, diagrams or the like, recorded oral instructions, instructions encoded on a fixed computer-readable medium, or any other instruction format suitable for conveying instructions for using the kit components to practice at least one method of the invention.

In one embodiment, a kit of the invention includes a label, and/or a packaging insert for detecting the presence of a neurotoxin in a subject or an environmental sample by determining the presence of BMAA or a BMAA derivative. In one embodiment, a kit includes instructions for treating a subject in vitro, in vivo, or ex vivo. In additional embodiments, a kit includes a label or packaging insert including instructions for treating a subject in vivo, or ex vivo.

Instructions can include instructions for practicing immunoassays of the invention as described herein. The instructions may be on "printed matter," e.g., on paper or cardboard within the kit, on a label affixed to the kit or packaging material, or attached to a vial or tube containing a component of the kit. Instructions may comprise voice or video tape which can optionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can also include one or more detection means (e.g., detection enzymes and detection enzyme substrates, or other labelling moieties such as biotin and biotin-binding moieties, colloidal gold, fluorophores, dye groups, and the like) for detecting neurotoxic amino acids or derivatives according to the methods of the invention. Invention kits can additionally include a buffering agent, a preservative, or a stabilizing agent. The kit can further include control components for preparing standard curves and calibrating assays. Each component of the kit can be enclosed within a separate individual container. For example, a kit can include a single unit for detecting a neurotoxic amino acid, in particular BMAA, in a subject. Alternately, a kit can include multiple units for detecting neurotoxic amino acids in multiple samples. Alternately, a kit can include multiple units for detecting multiple neurotoxic amino acids, in a single sample or in multiple samples. Kit components can be in a mixture of one or more containers and all of the various containers can be within single or multiple packages.

In one embodiment, a kit includes one or more compositions for detecting the presence of a neurotoxin in a subject by measuring BMAA or a BMAA derivative in a tissue sample, packaged into suitable packaging material. In another embodiment, a kit includes one or more compositions for detecting the presence of a neurotoxin in an environmental sample by measuring BMAA or a BMAA derivative, packaged into suitable packaging material.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

Example 1

Antisera Raised Against BMAA

Polyclonal antibodies capable of recognizing BMAA were produced by methods adapted from protocols for producing and assessing polyclonal antibodies against the cyanobacterial hepatotoxin microcystin-LR (Metcalf et al. 2000, *Water Research* 32:2761-2769; Chu et al. 1989, *Appl Environ Microbiol* 55(8):1928-1933). Briefly, BMAA (molecular weight 118 Da) was conjugated to macromolecules to stimulate an immune response when introduced into a mammalian host, by adapting methods for antibody coupling as disclosed in Harlow and Lane, *Antibodies, A Laboratory Manual* (Cold Spring Harbor Laboratory, 1988). The carboxyl and amine functional groups at the chiral centre of BMAA were selected for conjugation to glutaraldehyde (GLU) and carbodiimide (EDC) linkers, to produce glutaraldehyde-BMAA (GLU-BMAA) and carbodiimide-BMAA (EDC-BMAA), respectively. GLU-BMAA and EDC-BMAA were each conjugated to keyhole limpet haemocyanin (KLH) or bovine serum albumin (BSA) to produce the following BMAA conjugates: BSA-GLU-BMAA (BGB); BSA-EDC-BMAA (BEB); KLH-EDC-BMAA (KEB); and KLH-GLU-BMAA (KGB).

Specifically, glutaraldehyde-coupled BMAA conjugates were prepared as follows. A 5 mg/ml solution of BMAA was prepared by adding an equal volume of double strength PBS to a 50 µl aliquot of BMAA (10 mg/ml in water). For KLH-GLU-BMAA (KGB), a solution of KLH was prepared at a concentration of 10 mg/ml in PBS. Forty (40) µl of BMAA was added to 1 ml KLH solution (10 mg/ml), followed by addition of 960 µl PBS. A 0.2% glutaraldehyde solution in PBS (~25% stock) was prepared. An equal volume of glutaraldehyde was slowly added to the carrier protein-BMAA solution with constant agitation, then incubated for 1 hour at room temperature. Glycine from a 1M stock in PBS (pH 7.4) was to a final concentration of 200 mM, and incubated with stirring for 1 hour. The KGB conjugate was separated from other reactants by dialysis against PBS (4 changes of 2 L, overnight). After dialysis, the protein concentration of the solution containing the KLH conjugate was determined and KGB was stored in 500 µg aliquots at −20° C.

For BSA-GLU-BMAA (BGB), the same procedure was used, starting with a 10 mg/ml solution of BSA. After dialysis, the protein concentration of the solution containing the BSA conjugate was determined and BGB was stored in 500 µg aliquots at −20° C.

EDC-coupled BMAA conjugates were prepared as follows. Fifty (50) µl of the BMAA stock (5 mg/ml) was added to a microcentrifuge tube. A solution of EDC (1-ethyl-3-(3-dimethylaminopropyl) carbodiimide hydrochloride at a concentration of 11.1 mg/ml in PBS was prepared, and 450 µl of the EDC solution was added to the BMAA solution and adjusted to pH 8 using 0.1M NaOH. The mixture was incubated for 5 minutes at room temperature, and the pH was checked and adjusted with NaOH if necessary. For KLH-EDC-BMAA (KEB), one (1) ml of a solution containing the KLH carrier protein at a concentration of 10 mg/ml was added to the EDC-BMAA solution and the mixture was incubated at room temperature for 4 hours. The reaction was stopped by adding sodium acetate (pH 4.2) to a final concentration of 100 mM (for 1.1M stock, 150 µl was added). The mixture was incubated at room temperature for 1 hour. The KEB conjugate was separated from other reactants by dialysis against PBS (four changes of 2 L overnight). After dialysis, the protein concentration of the solution containing the KLH conjugate was determined and KEB was stored in 500 µg aliquots at −20° C.

For BSA-EDC-BMAA (BEB), the same procedure was used, starting with a 10 mg/ml solution of BSA. BEB conjugates were separated from other reactants after coupling by dialysis as described above, the protein concentration of the solution containing the BSA conjugate was determined, and BEB was stored in 500 µg aliquots at −20° C.

The KLH-BMAA conjugates, i.e., KLH-EDC-BMAA (KEB) and KLH-GLU-BMAA (KGB), were selected for use in immunizations to raise antisera. BSA-BMAA conjugates, i.e., BSA-EDC-BMAA (BEB) and BSA-GLU-BMAA (BGB), were used for coating immunoassay plates to test antisera and develop immunoassays.

New Zealand White rabbits were injected with KLH-EDC-BMAA (KEB) or KLH-GLU-BMAA (KGB) in accordance with standard protocols (Metcalf et al., 2000). Briefly, a rabbit received a subcutaneous primary injection of a solution containing BMAA-KLH conjugate (KEB or KGB) and Freund's Complete Adjuvant, and an intravenous booster injection 2 weeks later. Additional antigen booster injections were performed at 1-month intervals, with serum harvesting (approx. 20 ml blood) at one week after each booster injection. The harvested blood was allowed to clot and stored overnight, prior to separation of serum from red blood cells. Isolated serum underwent three (3) ammonium sulphate precipitations prior to dialysis against PBS. Aliquots (100 µl) of each serum sample, including pre-immune serum ("null serum"), were stored at −20° C. until required. One rabbit was immunized with KGB, and serum was harvested at eight (8) different time points (8 "bleeds"). A total of two rabbits were immunized with KEB, where the first rabbit died after the second bleed, and a second rabbit was then immunized with KEB and serum was harvested at 5 different time points (5 "bleeds") from the second rabbit. In order to allow differentiation of results using sera from the two rabbits immunized with KEB, sera from the first rabbit immunized with KEB was identified as "KLH-EDC1-BMAA" antiserum, and sera from the second rabbit immunized with KEB, was identified as "KLH-EDC2-BMAA" antiserum.

Example 2

Preliminary Characterization of Antisera Raised Against BMAA

Preliminary measurements indicated that the immune sera included antibodies that were reactive with BMAA, in addition to antibodies reactive with the carrier protein(s) and cross-linker(s).

Antibody Capture Immunoassay

Antibody capture immunoassays similar to those shown to be successful for characterizing antisera raised against microcystins (Metcalf et al., 2000; Chu et a/.1989), were used to characterize the antisera raised against BMAA conjugates prepared as described above. Here, binding of rabbit antibodies was detected using anti-rabbit secondary antibodies labelled with horseradish peroxidase (HRP), and the chromogenic synthetic HRP substrate 3,3',5,5'-tetramethylbenzidine (TMB). After wells were coated with BMAA conjugate (100 µl per well), plates were washed and blocked with 1% (w/v) dried milk powder in PBS (Marvel brand, 180 µl per well). After blocking, the plates were incubated at 37° C. for 1 hour before further washing, followed by application of primary antibody (in PBS). After addition of primary antibody and incubation, each plate was washed and goat-anti-rabbit IgG-HRP (Sigma) at a 1/10000 dilution in PBS was added to the wells (100 µl per well). The plates were then incubated for 1 hour at 37° C., and then washed. HRP substrate TMB was added to each well (100 µl per well) and the plates were allowed to develop for 30 minutes at room temperature. The HRP-TMB reaction was stopped by the addition of 100 µl 1M HCl, and the absorbance at 450 nm ($A_{450}$) of each well was measured to determine the amount of bound antibody in each well.

Here, BSA-BMAA conjugates were coated on wells of immunoassay plates at various coating concentrations, samples of antisera raised against the BSA-BMAA conjugates prepared by the same method were added to the immunoassay plates (i.e., antisera raised against BEB was added to BEB-coated wells, and the same pattern for BGB), and antibodies were captured by binding to the BSA-BMAA conjugates coated on the plates, wherein antibody binding was measured using goat-anti-rabbit-IgG-HRP secondary antibodies, TMB substrate, and measurement of $A_{450}$ for each well. BMAA-coated wells were also probed using null serum obtained from a rabbit prior to immunization with the BMAA conjugate that was used to coat the wells, where null sera were purified as described above.

Using a different experimental approach to antibody capture immunoassays, BMAA was bound directly to the surfaces of the wells (i.e. not through BSA or KLH conjugates), and anti-BMAA antibody binding was measured as described above. The effect of pH and plate format on antibody capture was measured using solutions having different pH values, and with BMAA directly bound to multi-well plastic plates of various formats known to have different binding characteristics at different pH values. BMAA (20 µg/ml) was dissolved in buffers having different pH values: acetate at pH 4; PBS at pH 7.4; carbonate at pH 9.6. The BMAA solution was then coated on plates known to have pH-specific binding characteristics: Nunc brand MAXISORP™, Nunc brand MEDISORP™, and Nunc brand MULTISORP™ plates (Thermo Fisher Scientific). An aliquot of antiserum raised against a BMAA conjugate, or null serum (pre-immune serum), each at 1/1000 dilution, was then added to each well, in a design that tested each serum sample against each plate format/pH combination. The following serum samples were tested for binding to different plates formats at different pH values: two (2) null serum samples from two different rabbits (NS1, NS2); two (2) antisera raised against KLH-EDC-BMAA in different rabbits, where EDC1-1 was the first bleed from first BMAA-EDC-immunized rabbit before it died, and EDC2-1 was the first bleed from second BMAA-EDC-immunized rabbit; and four (4) successive "bleeds" of antisera raised against KLH-GLU-BMAA (Glu1, Glu2, Glu3, Glu4), taken at monthly intervals from the same rabbit. Although the format with BMAA bound directly to the surfaces of the wells gave absorbance readings that were significantly higher in each well where antiserum against a BMAA conjugate was added, compared with the absorbance readings of wells with null serum (NS) added, this format was not used for further studies.

Verification of Specificity for BMAA Portion of BMAA Conjugates

Antisera raised against BMAA conjugates were tested to verify the presence of BMAA-specific antibodies, i.e., to verify the presence of antibodies that react with the BMAA portion of the BMAA conjugates used to induce the immune reaction to produce the antisera. Here, antisera raised against KLH-BMAA conjugates were tested for the ability to bind to BSA-BMAA conjugates synthesized using the "opposite" cross-linking chemistry. BSA-BMAA conjugates were used to detect BMAA-specific antibodies because it was expected that the rabbit antisera raised against KLH-conjugated immunogens would not have antibodies against BSA. Further, it was understood that, as a result of conjugating BMAA to the carrier protein (KLH) using different cross-linking chemistries (GLU, EDC), steric changes in the conformation of the BMAA molecule would be expected. Thus, it was expected that antisera raised against BMAA conjugated via one cross-linking chemistry, might show lower reactivity against BMAA conjugated via the "opposite" cross-linking chemistry.

When antisera raised against KLH-BMAA conjugates were tested against BSA-BMAA conjugates prepared using both cross-linking chemistries, each antiserum showed a positive reaction against BSA-BMAA conjugated via the "opposite" cross-linking chemistry. That is, antisera raised against EDC-linked BMAA conjugates (KEB) showed a positive reaction against GLU-linked BSA-BMAA (BGB). Likewise, antisera raised against GLU-linked BMAA conjugates (KGB) showed a positive reaction against EDC-linked BSA-BMAA (BEB). As expected, each antiserum showed a positive reaction against BSA-BMAA conjugated via the same cross-linking chemistry as the BMAA conjugate that was used to raise the antiserum. It was noted that antisera raised against KGB appeared to react more strongly to EDC-cross-linked samples, compared with antisera raised against KEB reacting to GLU-cross-linked samples. The first animal immunized with KEB yielded antiserum (KLH-EDC1-BMAA) that produced a better response than the antiserum of the second animal immunized with this conjugate (KLH-EDC2-BMAA)

These results indicated that BMAA specific antibodies were present in the IgG pool of harvested antisera, and the cross-linking method used for conjugation had no detectable negative effect on the ability of antisera to recognize BMAA.

Reactivity of Antisera with Free BMAA Determined Using Indirect Competitive ELISA The ability of antisera raised against BMAA conjugates to bind free BMAA was determined using an indirect competitive ELISA format modified from the antibody capture immunoassay described above. That is, antibody capture immunoassay was carried out generally as described above for plates with BSA-BMAA conjugates bound to the wells, except that free BMAA (unbound and unconjugated) and antisera were added to each well at the same time, such that free BMAA in solution and bound BSA-BMAA conjugates on the wells competed for antibody binding.

Briefly, each assay well was coated by addition of 100 µl of BSA-BMAA (BGB or BEB) in PBS, pH 7.4, and incubation for 1 hour at 37° C., using BSA-BMAA concentrations of 2 µg/ml, 1 µg/ml, or 0.5 µg/ml. Wells were then blocked with 1% (w/v) dried milk powder in PBS (Marvel brand, 180 µl per well). "Primary antibody" solution containing included free BMAA (50 µl/well L-BMAA, 10 µg ml$^{-1}$ in MilliQ water) and antiserum against KLH-conjugated BMAA (anti-KEB or anti-KGB, 50 µl/well diluted in PBS) was added to each well, using antiserum at dilutions of 1/1000, 1/5000, 1/10000, 1/50000, and 1/1000000 (i.e., 1/1×10$^6$). Antibody binding to BSA-BMAA coated on wells was detected using goat-anti-rabbit IgG-HRP (Sigma) at 1/10,000 in PBS (100 µl/well), washing and addition of TMB substrate (KPL Laboratories, 100 µl/well). The HRP/TMB reaction was then stopped by addition of 100 µl/well 1M H$_2$SO$_4$ and the amount of bound antibody was determined by measuring absorbance at 450 nm ($A_{450}$). The ability of free BMAA to compete with bound BSA-BMAA conjugates for antibody binding, i.e., binding to free antigen (free BMAA), was reported as the % $B_0$ value calculated as a ratio of $A_{450}$ values using the following equation:

% $B_0$=(Absorbance of test samples/Absorbance of control)×100

"Control" values were measured in wells to which no free BMAA was added. A % $B_0$ value of less than 100 (<100) indicated that in the test samples, some of the antibody had bound to free BMAA in solution and the amount of antibody binding to the BSA-BMAA conjugates coated on the wells was thereby reduced. That is, a value of % $B_0$<100 indicated that antibodies in the antiserum had detected and bound free BMAA.

Preliminary assessments were performed using antiserum raised against KLH-BMAA conjugates and wells coated with BSA-BMAA conjugates having the same cross-linking chemistry and different cross-linking chemistry as the KLH-BMAA conjugate. Assays using the same cross-linking chemistry were carried out using: (A) anti-KGB antiserum from bleed 3 (GLU AS) added to wells coated with BGB; and (B) anti-KEB antiserum from EDC rabbit 2, bleed 2 (EDC 2 AS) added to wells coated with BEB. Assays using different cross-linking chemistry were carried out using: (A) anti-KGB antiserum from bleed 3 (GLU AS) added to wells coated with BEB; and (B) anti-KEB antiserum from EDC rabbit 2, bleed 2 (EDC 2 AS) added to wells coated with BGB. Free BMAA, antiserum dilutions, coating concentrations, and reaction conditions were as described above.

In assays using the same cross-linking chemistry, little binding to free BMAA was detected, with the exception of antiserum raised against KGB (GLU AS) at 1/1000 dilution, which had a % $B_0$ value of 98% in wells coated with 2 µg/ml BGB, and antiserum raised against KEB (EDC 2 AS) at 1/50,0000 dilution, which had a % $B_0$ value of 80% in wells coated with 2 µg/ml BEB, although reproducibility was problematic.

In assays using different cross-linking chemistries, detection of binding to free BMAA improved. Values of % $B_0$<100% were measured in the majority of the assays, indicating that antibodies in the antiserum were binding to free BMAA in solution instead of binding to BSA-BMAA conjugates coated on the assay plate wells. Antiserum raised against KGB (GLU AS) had values of % $B_0$ as low as 80% in wells coated with BEB. Antiserum raised against KEB EDC 2 AS) had values of % $B_0$ as low as 70% in wells coated with BGB. These results indicated that antisera raised against KLH-BMAA conjugates could detect free BMAA, i.e. the antisera included antibodies that specifically reacted with free BMAA.

Clean-Up of Antisera by Immunoprecipitation with KLH

After the experiments described above indicated that antisera raised against KLH-BMAA conjugates could detect free BMAA, a clean-up procedure was developed to remove extraneous components such as antibodies against the KLH carrier protein and the cross-linking molecules. When a hapten of interest is crosslinked to a carrier protein and the hapten-crosslinker-carrier protein complex is used for immunization, it is expected that the mammalian immune system will produce antibodies against all parts of the complex, including the cross-linking molecule and the carrier protein. Thus, it is often considered beneficial to carry out further clean-up steps to remove or reduce the antibodies against non-hapten epitopes, thereby increasing the relative abundance of anti-hapten antibodies in the antiserum preparation. Suitable methods include immunoprecipitation or use of immunoaffinity columns.

Immunoprecipitation using KLH was carried out to remove antibodies against KLH as follows: a 1 µg aliquot of KLH was added to a stabilized antiserum preparation (antibody solution); the mixture was allowed to react for 30 minutes at 37° C.; the mixture was centrifuged and the supernatant was transferred to fresh tubes for the next immunoprecipitation using a fresh 1 µg aliquot of KLH. At each immunoprecipitation, an aliquot of the antiserum was removed and tested for reactivity against KLH and against BSA-BMAA conjugates. The results of KLH immunoprecipitation with both antisera (i.e., antiserum raised against GLU-linked BMAA (KGB) and antiserum raised against EDC-linked BMAA (KEB)) showed that the pool of antibodies against KLH could be removed and reactivity against BSA-BMAA conjugates remained in the partially purified "KLH-cleaned" antisera.

Fifteen (15) rounds of immunoprecipitation with KLH were carried out on antiserum raised against KGB, bleed 3 (GLU AS) and an aliquot was taken after each round of immunoprecipitation and tested for reactivity against KLH at different concentrations, and reactivity against BSA-BMAA having the same cross-linking chemistry, namely BGB, at different concentrations.

Fifteen (15) rounds of immunoprecipitation with KLH were carried out on antiserum raised against KEB, second EDC rabbit, bleed 2 (EDC2 AS) and an aliquot was taken after each round of immunoprecipitation and tested for reactivity against KLH at different concentrations, and reactivity against BSA-BMAA having the same cross-linking chemistry, namely BEB, at different concentrations. For both antisera, results from tests of reactivity against KLH and BSA-BMAA showed that, over multiple rounds of immunoprecipitation, antibodies against KLH could be removed while the partially purified antiserum showed stable levels of reactivity against BSA-BMAA conjugates.

After 15 rounds of immunoprecipitation with KLH, each partially purified antiserum ("KLH-cleaned antiserum") was tested for reactivity against free BMAA in solution (1 µg/ml), using assay wells coated with BSA-BMAA conjugates having the same and different cross-linking chemistries, using the indirect competitive ELISA format to test for reactivity with free BMAA described previously. In this procedure, diluted antiserum was tested using free BMAA at 1 µg/ml in wells coated with: (1) BSA-BMAA conjugates with the same cross-linking chemistry as the cross-linking chemistry used to conjugate the KLH-BMAA used to raise the antiserum, and (2) BSA-BMAA conjugates of the opposite cross-linking chemistry as the cross-linking chemistry used to conjugate the KLH-BMAA used to raise the antiserum. The antisera were tested at dilutions of from 1/1000 to $1/1\times10^6$. Partially purified antisera detected free BMAA, as indicated by % $B_0$ values of 80-100%, compared to controls. Although it was determined that the partially purified antisera could react with free BMAA, it was further determined that the partially purified antisera had much greater affinity for BMAA conjugates. The partially purified antisera showed reactivity against free BMAA, with % $B_0$ values of between 80-100% compared with controls. It was further determined that the partially purified antisera had an affinity for BMAA conjugates greater than the affinity for free (unconjugated) BMAA.

Example 3

Reactivity of Anti-BMAA Antisera with BSA Conjugates of Structurally Similar Amino Acids Because BMAA is a derivative of alanine, and also has a structure similar to glutamic acid, experiments were carried out to determine whether antisera raised against BMAA showed reactivity with BSA-alanine and BSA-glutamic acid conjugates. Non-immunoprecipitated ("normal") and partially purified ("KLH-cleaned") antisera raised against BMAA conjugates KGB and KEB, were tested for reactivity with BSA-alanine and BSA-glutamic acid conjugates. The following GLU-linked and EDC-linked conjugates of BSA with alanine and glutamic acid were prepared and tested: BSA-GLU-alanine (BGA), BSA-EDC-alanine (BEA), BSA-GLU-glutamic acid (BGG) and BSA-EDC-glutamic acid (BEG).

Serial dilutions of "normal" and KLH-cleaned antiserum prepared as described above ("normal" antiserum was obtained prior to immunoprecipitation with KLH; KLH-cleaned antiserum included anti-KGB antiserum and anti-KEB antiserum, each after 15 rounds of KLH immunoprecipitation) and were tested for reactivity against each conjugate (BGA, BEA, BGG, BEG) by adding antiserum to wells coated with the various BSA-amino acid conjugates, and measuring antibody binding using the ELISA format described above. Both normal and KLH-cleaned antisera Both normal and KLH-cleaned antisera showed some reactivity with the BSA-glutamic acid conjugates and the BSA-alanine conjugates, but different patterns of reactivity were seen depending on cross-linking chemistry.

When the same cross-linking chemistry was used in the KLH conjugates used to raise the antisera, and the BSA conjugates used to test the antisera, both the "normal" and KLH-cleaned antisera showed reactivity with BSA-alanine and BSA-glutamate conjugates, in addition to the expected reactivity with BSA-BMAA conjugates. Both the normal and the KLH-cleaned samples of antisera raised against KGB (i.e. GLU-linked BMAA) had higher affinity for GLU-linked BMAA conjugates than for GLU-linked alanine or GLU-linked glutamic acid conjugates. In contrast, both normal and KLH-cleaned antisera against KEB (i.e., EDC-linked BMAA) recognized all three EDC-linked conjugates equally.

In contrast, when the opposite cross-linking chemistry was used in the KLH conjugates used to raise the antisera, and the BSA conjugates used to test the antisera (e.g. anti-KGB antisera tested for reactivity with BEB, BEA, and BEG), the antisera showed little reactivity with any of the conjugates Because antisera showed reactivity with (recognized) BSA-amino acid conjugates having the same cross-linking chemistry, these combinations were then used in the indirect competitive ELISA format to test for reactivity with free BMAA. That is, indirect competitive ELISA was used to measure the ability of free BMAA to compete for antibody binding in wells coated with BSA-amino acid conjugates. For each antiserum, the BSA-amino acid conjugates were cross-linked with the same cross-linking chemistry as the KLH-BMAA conjugate used to raise the antiserum. Thus, normal and KLH-cleaned antisera raised against KGB were tested for reactivity with free BMAA (1 µg/ml) in wells coated with BGB, BGA, or BOG. Normal and KLH-cleaned antisera against KEB were tested for reactivity with free BMAA (1 µg/ml) in wells coated with BEB, BEA, and BEG. For both cross-linking chemistries, the normal (non-immunoprecipitated) antiserum was able to detect free BMAA in solution, with % $B_0$ values of between 80% and 100%. However, KLH-cleaned antisera did not perform as well as normal (non-immunoprecipitated) antisera to detect free BMAA in solution, although free BMAA was detected in some assays.

Further Clean-Up by Immunoprecipitation with BSA-Alanine

Of the three BSA-amino acid conjugates tested (BSA-BMAA, BSA-alanine, BSA-glutamic acid), the BSA-alanine conjugates of both cross-linking chemistries (BGA, BEA) showed the lowest reactivity with antisera. Therefore, the KLH-cleaned antisera were further cleaned up by immunoprecipitation with BSA-alanine, in order to create antiserum preparations highly enriched in antibodies specific for BMAA alone. KLH-cleaned antisera prepared as described above (antiserum raised against KGB, bleed 3, after 15 rounds on immunoprecipitation; antiserum raised against KEB, second EDC rabbit, bleed 2, after 15 rounds of immunoprecipitation with KLH) were then subjected to an additional 14 rounds of immunoprecipitation with BSA-alanine.

After each immunoprecipitation (IP1 to IP14), each antiserum was tested for reactivity with BSA-BMAA conjugates, BSA-alanine conjugates, and BSA-glutamic acid conjugates, by adding antiserum to wells coated with the various BSA-amino acid conjugates and measuring antibody binding using the ELISA format described previously.

Antisera against KGB after immunoprecipitation with BGA, at a dilution of 1/1000 (the most concentrated solution tested), showed good reactivity against BGB, and lower reactivity against the other amino acid conjugates BGA and BGG, indicating that the antisera had specificity for BMAA. Reactivity with BGB declined during the first eight rounds of immunoprecipitation 1-8 (IP1 to IP8), and maintained a good level of reactivity during the final six rounds of immunoprecipitation (IP9 to IP14), while reactivity with BGA and BGG continued to decline with continuing rounds of immunoprecipitation. The trends in reactivity observed in this experiment suggested that antibodies that recognize the GLU crosslinker were being removed by immunoprecipitation with BGA.

Antisera against KEB, immunoprecipitated with BEA, at a dilution of 1/1000, showed a decrease in reactivity with all BSA-amino acid conjugates as immunoprecipitation proceeded. This result is in agreement with the results reported above, showing little difference in the ability of antisera raised against KEB (both "normal" and KLH-cleaned) to recognize specific BSA-amino acid conjugates.

After immunoprecipitation with BSA-alanine, antisera were then tested for their reactivity with free BMAA at 1 μg/ml, using the indirect competitive ELISA format described previously. Both immunoprecipitated antisera (antisera against KGB and antisera against KEB) showed little reactivity with free BMAA.

Example 4

Test of Specificity and Cross-Reactivity of Anti-BMAA Antisera Using Glutaraldehyde-Linked Coating Format Antisera produced as described above were tested using an adaptation of the immunoassay method of Ordronneau et al. (1991), representing an alternative method of coating amino acids and other haptens to microtiter plates for enzyme immunoassays. Ordronneau et al. disclosed that previous methods used assay substrates wherein the carrier proteins were coupled to the substrate and the amino acid or hapten was conjugated to the carrier protein, resulting in inconsistencies and difficulties in reproducibility and accuracy. Ordronneau et al. developed an immunoassay for glutamate (Glu) wherein Glu was linked directly to plastic surfaces via glutaraldehyde instead of being coupled to a carrier protein, and Glu-coated immunoassay plates were used to test antiserum raised against Glu.

The method of Ordronneau et al. was used to prepare immunoassay plates coated with glutaraldehyde-linked BMAA (no carrier protein) to test antisera of the present invention. Antiserum raised against KGB, third "bleed" was used for the experiment. The method of Ordronneau et al. was carried out using MAXISORP™ and MULTISORP™ plates coated with BMAA and glutamic acid, and anti-BMAA antisera (anti-KGB, bleed 3) at various dilutions from 1/1000 to 1/100,000, in the presence of BMAA at concentrations from 0 to 1 mM, or in the presence of glutamic acid at concentrations from 1 nM to 1 mM. MULTISORP™ plates showed higher absorbance values and better glutaraldehyde binding and subsequent BMAA binding. Antisera raised against KGB, at dilutions of 1/1000 1/2000, 1/5000, and 1/10000, showed increased binding to BMAA-coated plates when BMAA at higher coating concentrations (100 μM and 1 mM) had been added to the plate, presumably resulting in increased amounts of BMAA coated to the plates and available for antibody binding. No effect on antibody binding was seen with increasing concentrations of glutamate.

Figure 1:
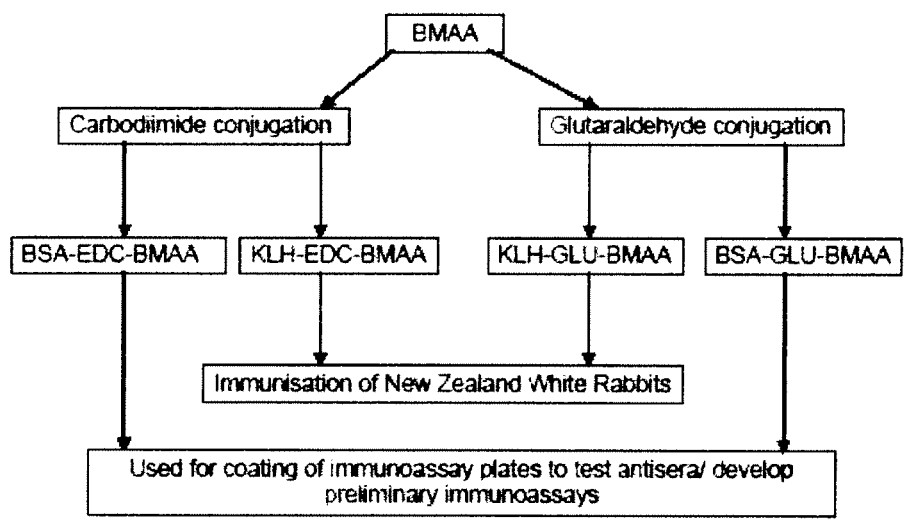
FIG. 1 shows an outline of the conjugation and immunization procedures used for production and testing of antibodies against BMAA, where KLH is keyhole limpet hemocyanin, BSA is bovine serum albumin, GLU is glutaraldehyde, and EDC is carbodiimide.
Figure 2:
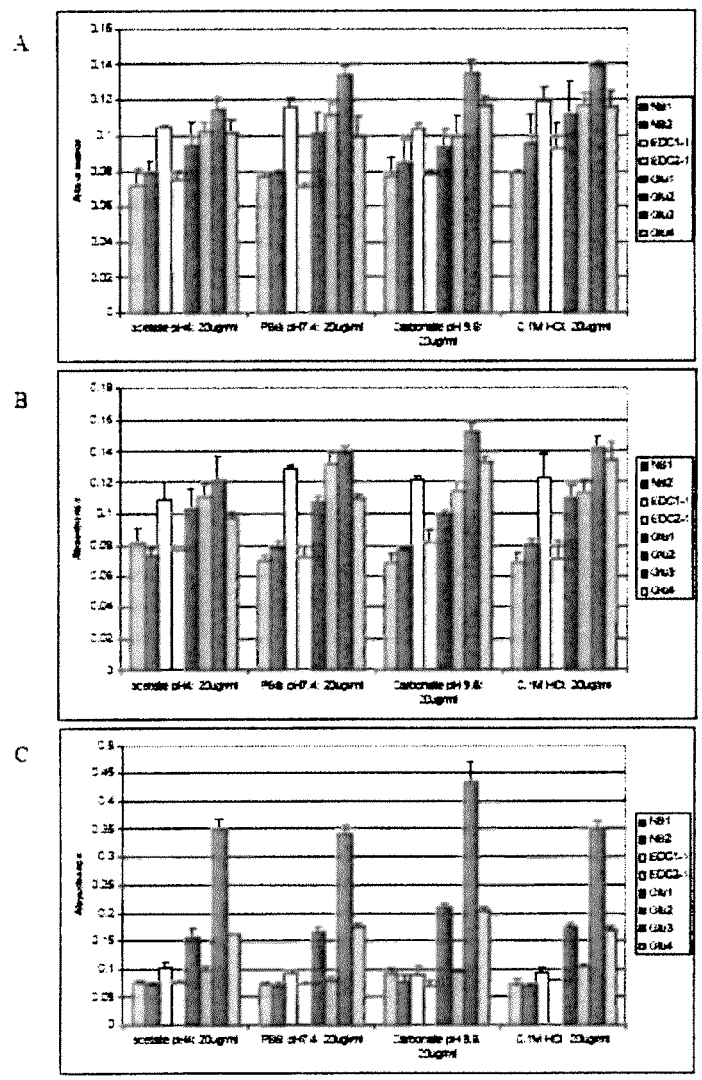
FIG. 2 shows results from antibody capture immunoassays to measure reactivity of antisera raised against BMAA conjugates (EDC1-1, EDC2-1, Glu1, Glu2, Glu3, Glu4) and null serum (NS1, NS2), with BMAA at a coating concentration of 20 μg/ml on MAXISORP™ (FIG. 3A), MEDISORP™ (FIG. 3B), and MULTISORP™ (FIG. 3C) plates in the presence of buffers having different pH values as shown.
Figure 3:
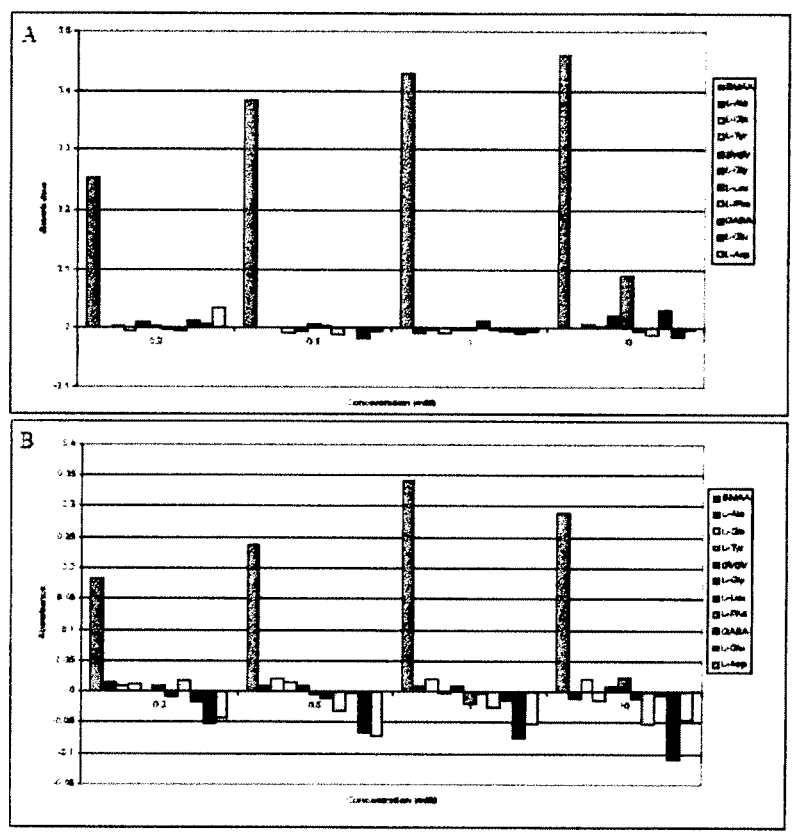
FIG. 3 shows results from antibody capture immunoassays to measure the reactivity of antisera raised against the BMAA conjugate KLH-GLU-BMAA (anti-KGB, bleed 3) at 1/1000 dilution (Panel A) and 1/2000 dilution (Panel B) with glutaraldehyde-linked BMAA, L-alanine (L-Ala), L-glutamine (L-Gln), L-tyrosine (L-Tyr), glycyl-glycine (glygly), L-glycine (L-Gly), L-leucine (L-leu), L-phenylalanine (L-Phe), gamma-aminobutyric acid (GABA), L-glutamic acid (L-Glu), and L-aspartic acid (L-Asp), at coating concentrations, from left to right, 0.2 mM, 0.5 mM, 1 mM and 10 mM.

Antiserum raised against KGB (anti-KGB antiserum), at dilutions of 1/1000 and 1/2000, was tested for cross-reactivity with BMAA and other amino acids, to test specificity for BMAA. Plates were coated, via glutaraldehyde linking, with BMAA, L-alanine (L-Ala), L-glutamine (L-Gln), L-tyrosine (L-Tyr), glycyl-glycine (glygly), L-glycine (L-Gly), L-leucine (L-leu), L-phenylalanine (L-Phe), gamma-aminobutyric acid (GABA), L-glutamic acid (L-Glu), and L-aspartic acid (L-Asp), at coating concentrations of 0.2 mM, 0.5 mM, 1 mM and 10 mM. As shown in FIG. 3, anti-KGB antiserum at both dilutions (1/1000 and 1/2000) showed strong recognition of BMAA and little cross-reactivity with the other amino acids tested. BMAA recognition by anti-KGB antiserum at 1/1000 dilution (FIG. 3A) increased with BMAA coating concentrations from 0.1 to 10 mM, i.e., signal strength increased with increasing BMAA to bind. BMAA recognition by anti-KGB antiserum at 1/2000 dilution (FIG. 3B) reached a plateau at 1 mM BMAA coating concentration, indicating that saturation binding had been reached at that concentration.

In this immunoassay format, anti-KGB antiserum at both dilutions showed strong recognition of BMAA and little cross-reactivity with the other amino acids tested, although anti-KGB antiserum at 1/1000 showed slight reactivity with L-glycine and glycyl-glycine, especially at a 10 mM coating (FIG. 3A), which was not entirely unexpected as L-glycine is used during the glutaraldehyde-cross-linked immunogen conjugation procedure to inactivate any remaining glutaraldehyde groups that may be present on the carrier protein. Of all the other amino acids tested, anti-KGB antiserum only showed slight reactivity with GABA at 10 mM, and L-aspartic acid at 0.2 mM. It was not determined whether conformational changes in these molecules upon binding to glutaraldehyde affected subsequent recognition by antibodies and further testing of "free" amino acids may be required for confirmation of these findings.

Example 5

Specificity of Anti-BMAA Antisera for BMAA from Different Sources; Determination of Isomer-Specific Reactivity The immunizations and immunoassays described above were performed with commercially available BMAA from Sigma (now Sigma-Aldrich Inc.; Cat. No. B107, Lot No. 097H4746). Immunoassays were performed again using two new, different batches of BMAA: one batch from a fresh lot of commercially available BMAA from Sigma (Lot 065K4707); and one batch of synthetic BMAA obtained from Peter Nunn at the University of Portsmouth, UK. Immunoassays using BMAA from each of the new batches, i.e., the fresh lot of BMAA from Sigma (Sigma-Aldrich, Lot 065K4707), and synthetic BMAA obtained from Peter Nunn (University of Portsmouth, UK), were carried out using the glutaraldehyde capture (glutaraldehyde-linked antibody capture form as described above), to measure the ability of various antisera to bind various targets such as BMAA from different batches.

Briefly, wells of a Nunc MULTISORP™ plate were washed with distilled water. Each well received 100 μl 0.5% glutaraldehyde in 100 mM NaH$_2$PO$_4$ (pH 4.5), and the plate was incubated at 37° C. for 1 hour. The plate was washed (i.e., each well of the plate was washed) twice with 180 μl 100 mM NaH$_2$PO$_4$ (pH 4.5). An aliquot of 100 μl of target, e.g. BMAA, prepared in 100 mM Na$_2$HPO$_4$ (pH 8), was added to each well and the plate was incubated at 37° C. for 1 hour. The plate was washed three times with 180 μl 100 mM Na$_2$HPO$_4$ (pH 8) each wash. An aliquot of 100 μl of 0.1M ethanolamine prepared in 100 mM Na$_2$HPO$_4$ (pH 8) was added to each well and the plate was incubated at 37° C. for 1 hour. The plate was washed three times with 0.05% Tween 20/PBS (PBST) each wash. An aliquot of 180 μl of 1% "Marvel" brand dry milk power in PBS was added to each well and incubated at 37° C. for 1 hour. The plate was washed three times with PBST. Dilutions of primary antibody in PBS were prepared, and 100 μl of (diluted) primary antibody was added to each well. The plate was incubated at 37° C. for 1 hour. The plate was washed three times with PBST. For detection, 100 μl of IgG-HRP (1/10000, Sigma goat-anti-rabbit IgG-HRP) was added to each well and the plate was incubated for 1 hour at 37° C. The plate was washed three times with PBST. For quantitation, HRP synthetic chromogenic substrate TMB was added (100 μl per well) and color was allowed to develop for 30 minutes at room temperature. The reaction was stopped by addition of 100 μl 1M H$_2$SO$_4$ and absorbance at 450 nm was measured for each well of the plate.

In one experiment, antiserum raised against KGB (anti-KGB antiserum), bleed 3, (KBG3) was cleaned up by precipitation with ammonium sulfate and immunoprecipitation with KLH by addition of 10 μg KLH to 100 μl antiserum, incubation for 30 minutes at 37° C., centrifugation at 2000×g for 5 minutes, and recovery of the supernatant, for use in ELISA or in further rounds of KLH immunoprecipitation. KLH-cleaned anti-KGB antiserum, at dilutions of 1/1000, 1/2000, 1/4000, 1/8000, 1/16000, and 1/32000, was added to plates with glutaraldehyde-linked BMAA from each of the two new batches of BMAA, at coating concentrations from 1 μM to 5 mM BMAA, and antibody binding to the plates measured. For both BMAA batches, the anti-KGB antisera showed increasing signal strength (reactivity) with increasing BMAA coating concentration, which confirmed that the anti-KGB antiserum contained antibodies specific for BMAA. The immunoassay used here had a detection limit of 10 μM BMAA, and maximal reactivity (maximal absorbance) was measured at a BMAA coating concentration of 0.5 mM for both BMAA batches.

The signal strength (reactivity) of different antiserum dilutions for each BMAA coating concentration was determined for each of the two different batches of BMAA, and correlation coefficients were calculated from a plot of the values from the fresh lot of BMAA from Sigma on x-axis, against the values from synthetic BMAA from P. Nunn on y-axis. Separate regression analyses were carried out, and correlation coefficients were calculated, for the 1/1000 dilution, the 1/200 dilution, and the 1/4000 dilution of anti-KGB antiserum. The correlation coefficients showed a positive correlation between the different BMAA batches (>0.89). However, the slope of the regression lines for each anti-KGB antiserum dilution indicated that the signal obtained using the same antiserum dilution and the same BMAA coating concentration, was twice as high for the fresh lot of BMAA from Sigma as the signal obtained using the synthetic BMAA from P. Nunn (University of Portsmouth, UK). The 1/1000 dilution had a regression line slope of 0.65, the 1/2000 dilution had a regression line slope of 0.56, and the 1/4000 dilution had a regression line slope of 0.49.

It should be noted that, although BMAA from all sources were synthetic products, each product had a different isomer composition. The synthetic BMAA from Sigma Lot No. 097H4746, which was used as the original antigen for conjugation and immunization, was described by the manufacturer as containing greater than 94% L-isomer. The BMAA supplied by Peter Nunn (University of Portsmouth, UK) was described as containing a mixture of D- and L-forms in approximately equal amounts, with a slight preponderance of the L-isomer (Peter Nunn, personal communication). Results from regression analysis (see above) were evaluated in light of the different isomer composition of each product, and these results indicated that the antisera raised against KGB prepared using BMAA from Sigma Lot No. 097H4746 which was predominantly L-isomer (>94% L-isomer), preferentially bound to glutaraldehyde-captured L-BMAA isomer, and showed little reactivity with the D-isomer of BMAA. Under these conditions, the antisera bound to L-isomer of BMAA and did not substantially bind the D-isomer of BMAA.

After isomer-specific reactivity of unpurified antiserum raised against KGB ("normal" antiserum) had been demonstrated, the reactivity of normal anti-KGB antiserum was compared with the reactivity of partially purified "KLH-cleaned" anti-KGB antiserum and partially purified "alanine-cleaned" anti-KEB antiserum. All antisera were used at dilutions of 1/1000 and 1/2000, to test binding to BMAA in wells at coating concentrations of 1 μM to 5 mM, and free BMAA was present at 500 μM. Both the unpurified "normal" anti-KGB antiserum and the partially purified KLH-cleaned anti-KGB antiserum showed increased binding to BMAA-coated plates with increasing BMAA coating concentrations up to 0.5 mM BMAA. Both dilutions (1/1000 and 1/2000) of unpurified "normal" anti-KGB antiserum showed slight decreases in binding at coating concentrations of about 0.5 mM BMAA. Both dilutions of KLH-cleaned anti-KGB antiserum showed a plateau in binding at coating concentrations between 0.5 mM to 5 mM BMAA, which may have indicated limited antibody accessibility and/or binding saturation at coating concentrations above 0.5 mM BMAA. In contrast, alanine-cleaned anti-KEB antiserum, at dilutions of 1/1000 and 1/2000, showed no detectable binding to BMAA (i.e. to BMAA-coated plates) at any coating concentration from 1 μM to 5 mM BMAA.

Unpurified "normal" anti-KGB antiserum (bleed 3) was tested to determine its ability to bind free BMAA, using the glutaraldehyde-capture immunoassay described above, modified for an indirect competitive binding assay. Test wells were coated with glutaraldehyde-linked BMAA coating concentrations of 50 μM, 200 μM, 500 μM, 1 mM, and 5 mM BMAA. Free BMAA at a concentration of 500 μM, and normal anti-KGB antiserum (bleed 3) at dilutions of 1/1000, 1/2000, and 1/4000, were added to test wells, antibody binding to glutaraldehyde-linked BMAA in the wells was determined, and the % $B_0$ value was calculated as described above to determine the reactivity of antisera with free BMAA. In the present experiment, antisera were able to detect (react with) free BMAA (i.e., % $B_0$<100) in the majority of assays. The results showed a general trend in which the % $B_0$ value appeared to decrease with increasing BMAA coating concentration, or with increasing antiserum concentration (lower antiserum dilution). The largest % $B_0$ value measured was 56%, indicating a 44% reduction in antibody binding to the BMAA coated on the wells, due to antibody binding to free BMAA.

Example 6

Amplification Systems for Detecting Anti-BMAA Antibody Binding

Experiments described above established that antisera raised against BMAA conjugates included antibodies that have apparent isomer-specific reactivity with L-BMAA and little cross-reactivity with other amino acids, wherein the antiserum could be used to detect free BMAA at a concentration of approximately 500 µM (59 µg ml-1). Experiments as described below were carried out to evaluate various amplification systems for their ability to improve the signal and detectability of free BMAA without the requirement for further purification of the antisera.

Amplification of Anti-BMAA Antibody Signals

Immunoassay sensitivity was increased by using a VECTASTAIN™ ABC-Peroxidase kit (VECTASTAIN™ ABC Elite kit for rabbit IgG, Cat. No. PK-6101, Vector Laboratories, Burlingame Calif.) to generate a horseradish peroxidase (HRP) detection complex with a higher number of detection enzymes, resulting in greater color development (stronger signal) upon addition of substrate, and a higher absorbance value compared to standard assay using HRP-coupled IgG (IgG-HRP). By using the VECTASTAIN™ system with increasing BMAA coating concentrations in an antibody capture immunoassay, measurement of a significantly stronger (increased) signal was possible, as compared with the signal measured with a standard IgG-HRP as described in experiments above. However, the background signal was also significantly enhanced by the VECTASTAIN™ system, necessitating the development of appropriate controls to be used when assessing antisera.

The VECTASTAIN™ system was used in a glutaraldehyde-linked antibody capture assay as described above, in an indirect competitive assay format, to measure the effect of different glutaraldehyde concentrations, different free BMAA concentrations, and different antiserum dilutions, on the ability of unpurified normal anti-KGB antiserum to detect free BMAA. The two glutaraldehyde concentrations tested for effects on BMAA coating were 0.2% glutaraldehyde and 0.5% glutaraldehyde. Wells were coated with BMAA, through a glutaraldehyde linkage, using BMAA coating solutions of 100 mM, 50 mm, and 20 mM BMAA. Antiserum raised against KGB, third bleed (KGB3) was used at concentrations of 1/8000, 1/16000, and 1/20000. Free BMAA was added to wells at concentrations of 1 µg/ml and 10 µg/ml; controls wells had no free BMAA added. In the design of the experiment, antiserum at 1/8000 was tested for reactivity with both levels of free BMAA, i.e. the experiment included antiserum at 1/8000 incubated with 1 µg/ml free BMAA and antiserum at 1/8000 incubated with 10 µg/ml free BMAA. Antiserum at 1/16000 dilution and 1/20000 dilution were only incubated with 10 µg/ml free BMAA. VECTASTAIN™ amplification system was used as described above, to amplify the results. % $B_0$ values were calculated with and without correcting for blanks.

Results from all experimental designs showed that the anti-KGB antisera contained antibodies that reacted with free BMAA, i.e. % $B_0$<100 indicating that antibodies bound to free BMAA did not bind to glutaraldehyde-linked BMAA coating the wells. The effect of free BMAA was most pronounced for antiserum at 1/16000 and 1/20000 dilutions, when incubated with 10 µg/ml free BMAA. At both glutaraldehyde concentrations tested for their effects on BMAA coating of wells (i.e. 0.2% and 0.5% glutaraldehyde), the assay showed that free BMAA at concentrations of 1 μg/ml and 10 μg/ml could be detected by the immunoassay, both before and after correcting % $B_0$ values for blanks.

Additional Modifications to Alter Immunoassay Sensitivity

The previous standard immunoassay system that showed unpurified "normal" anti-KGB antiserum could detect free BMAA at 59 μg/ml, and use of the VECTASTAIN™ amplification system provided improved detection. Additional developments and modifications were carried out to further improve the sensitivity of a potential BMAA immunoassay, in particular chemical modifications such as biotinylation.

Biotin-avidin amplification in combination with VECTASTAIN. The biotin-avidin reaction is one of the highest affinity reactions known, and biotinylated probes can be quickly and specifically attached to enzymes or solid phases using avidin systems. Biotinylated BMAA probes were produced as described below, and used in combination with the avidin-HRP complex from the VECTASTAIN™ kit, in an attempt to improve the sensitivity and specificity of the BMAA immunoassay.

Reactivity of Biotin-BMAA with Anti-BMAA Antisera Using Direct ELISA

Biotinylated BMAA was tested using an ELISA design in which the wells were coated with antiserum at various dilutions, various amounts of biotinylated BMAA was added to the wells, and the binding of biotinylated BMAA to immobilized antibody was measured. Because the purpose of the assay was to determine whether biotin-BMAA conjugates were feasible for use in a BMAA immunoassay, and to determine whether biotinylated BMAA would bind to antisera raised against BMAA conjugates, the ELISA was a straightforward antibody binding assay, and no free BMAA was used.

Briefly, antisera raised against KEB and KGB were coated on assay plates, a biotin-BMAA probe at various dilutions was added to the antiserum-coated wells, and biotin-BMAA binding to immobilized antibody in each well was measured using avidin conjugated to a chromogenic marker, e.g. HRP.

Biotinylated BMAA was prepared as follows. A solution of BMAA at a concentration of 1.18 mg/ml in PBS was prepared. A biotin (with linker) solution was prepared using sufficient EZ-link Sulfo-NHS-LC-LC-biotin to prepare a solution of 6.99 mg $ml^{-1}$ in PBS. For mixing and labelling, 1 ml of BMAA was mixed with 1 ml biotin solution, and the components were allowed to react at room temperature before being used in ELISA. A 1M stock solution of BMAA-biotin (biotinylated BMAA) was prepared, and dilutions were made on a volume basis. Stock solution of biotin-BMAA at 1M was used at vol/vol dilutions of 1/100 (0.01M), 1/500 (0.002M), 1/1000 (0.001M), 1/5000 (0.0002M), 1/10000 (0.0001M), 1/50000 (0.00002M), and 1/100000 (0.00001M).

The following antisera were used: anti-KEB antiserum, sixth bleed from the second rabbit immunized with KEB (EDC6, sixth bleed from rabbit KLH-EDC2-BMAA); anti-KGB antiserum, ninth bleed (GLU9). Each antiserum represented a single harvest (a single "bleed") and was subjected to an initial partial purification by ammonium sulphate precipitation. Antisera were diluted to 1/1000, 1/5000, and 1/10000 in PBS before being used in ELISA as described below.

For ELISA, wells were coated with antisera by adding a 100 μl aliquot of diluted antiserum and incubating the plate for 1 hour at 37° C. The plate was washed 3 times with PBST. Wells of the plate were blocked with 180 μl 1% Marvel dry milk power in PBS, and the plate was incubated for 1 hour at 37° C. The plate was subsequently washed three times with PBST before addition of the biotin-BMAA conjugates to the plate. The plate was incubated for 1 hour at 37° C. before three washes with PBST. A 100 μl aliquot of the avidin-HRP complex provided with the VECTASTAIN™ amplification kit was added to each well, followed by incubation for 1 hour at 37° C. The plate was washed three times with PBST before addition of TMB substrate for 30 minutes at room temperature (100 µl per well). The reaction was stopped by the addition of 1M $H_2SO_4$ (100 µl) and absorbance at 450 nm was measured for each well.

BMAA-binding to immobilized antibodies (antisera) showed a strong signal-dose response, where the signal strength decreased ($A_{450}$ indicating antibody binding to BMAA-biotin probes) decreased as the "dose" of BMAA-biotin probe decreased. Both antisera (anti-KEB and anti-KGB) at all dilutions (1/1000, 1/5000, and 1/10000) showed the same signal-dose pattern of decreasing signal strength with decreasing BMAA-biotin (i.e. increasing BMAA-biotin dilution).

Different detection probes: single (unamplified) avidin-HRP probes. In another experiment, different commercially available single (unamplified) HRP-avidin probes were used to detect BMAA-biotin probes bound to immobilized antibodies from anti-KGB antiserum, as an alternative to using the VECTASTAIN™ HRP-avidin complex. ELISA was carried out as described above. Briefly, anti-KGB antiserum (bleed 9, see above), was coated on assay plates at a dilution of 1/1000, and biotin-BMAA at dilutions of from 1/100 (0.01M) to 1/100000 (0.00001M) as above, was added to wells. Commercially available single HRP-avidin probes (Sigma-Aldrich, Cat. No. 1-3151, at 250 µg/ml) were tested for the ability to detect binding of biotin-BMAA to immobilized antibody. Avidin-HRP was diluted to provide solutions of different strengths: avidin-HRP diluted (vol/vol) 1/1000, 1/2000, 1/4000, and 1/6000. Each biotin-BMAA concentration was measured using each dilution of avidin-HRP.

Strong signal-dose responses were observed using single avidin-HRP probes. For each biotin-BMAA concentration (dilution), the strongest signal was seen in assays using the HRP-avidin probe at 1/1000 dilution, i.e., the highest concentration of HRP-avidin probe. For each biotin-BMAA dilution, signal strength decreased with HRP-avidin concentration, i.e., the signal decreased as the HRP-avidin probes were increasingly diluted.

Reactivity of Anti-BMAA Antisera with Free BMAA in the Presence of Biotin-BMAA

Assay wells were coated with biotin-BMAA at different dilutions, and commercially available single HRP-avidin probes at different dilutions, were used in an indirect competitive ELISA format to detect reactivity of anti-KGB and anti-KEB antisera with free BMAA at a concentration of 5 µg/ml. Both anti-KGB and anti-KEB antisera showed reactivity with 5 µg/ml free BMAA, as demonstrated by measured values of % $B_0$<100, with the strongest reaction seen with anti-KGB antisera having a % $B_0$ value as low as 78%.

Example 7

Use of Anti-BMAA Antibodies to Detect BSA-BMAA Conjugates on Immunoblots

It is understood that BMAA may be associated with peptides and proteins in various ways, including physical attachment to or association with the surface of peptides, and/or incorporation of BMAA into polypeptide chains. Experiments described above indicated that antisera raised against KLH-BMAA conjugates (anti-KGB and anti-KEB antisera) contain antibodies capable of recognizing BMAA in conjugated and free formats (i.e., conjugated BMAA and free BMAA). Therefore, antisera raised against BMAA conjugates as described above were used to detect the association of BMAA with polypeptides on immunoblots (Western blots). In certain experiments, the antisera were used to probe immunoblots (Western blots) of various protein preparations, to determine whether these antisera could recognize protein-associated BMAA.

As demonstrated in experiments described above, anti-KGB and anti-KEB antisera were capable of recognizing BMAA-BSA conjugates. Therefore, anti-KGB and anti-KEB antisera were used to probe Western blots of BSA and various BSA-BMAA conjugates. The following samples were subjected to SDS gel electrophoresis and were transferred to a membrane for Western blot (immunoblot) analysis: BSA-GLU-BMAA (BGB), BSA-EDC-BMAA (BEB), and unconjugated BSA (native protein). Results from immunoblots using antisera raised against KLH-conjugated BMAA to probe blots of BSA-BMAA conjugates showed promising indications for detection of BMAA chemically bound (conjugated) to the surface of large molecular weight proteins (e.g. BSA) on immunoblots.

Proteins were loaded on a polyacrylamide gel (10 µg protein per lane) and subjected to electrophoresis through a 4% stacking gel followed by a 12% separating gel, at 200V for approximately 40 minutes, using a BioRad Mini-PROTEAN® II (BioRad, Hercules Calif.).

Proteins were transferred from polyacrylamide gels to nitrocellulose membranes overnight at room temperature (BioRad Mini Trans-Blot®, BioRad, Hercules Calif.) as follows. Transfer buffer (3.03 g Tris, 14.4 g glycine, 200 ml methanol; made up to 1 L with water) was prepared and stored at 4° C. Each nitrocellulose membrane was cut to fit the dimensions of the gel from which proteins were to be transferred. All components were pre-wetted and equilibrated prior to transfer by soaking the gel(s), nitrocellulose membranes, filter paper, and fiber pads in transfer buffer. The "sandwich" was prepared by opening the holder cassette with the outer (grey) side on a clean surface, placing a pre-wetted fiber pad on the grey side of the cassette, placing a sheet of filter paper on the fiber pad, placing the equilibrated gel on the filter paper, taking care to remove bubbles, placing the pre-wetted nitrocellulose membrane on the gel, taking care to remove air bubbles, placing filter paper on the nitrocellulose membrane, adding the last fiber pad, and closing the holder cassette. After adding the cooling unit and filling the tank completely with transfer buffer, the transfer was effected at 30V, 90 mA, overnight (approximately 18 h). After transfer was deemed complete, the quality of transfer and location of protein bands could be visualized by reversible staining with Ponceau S. If desired, membranes were marked during this step.

Figure 4:
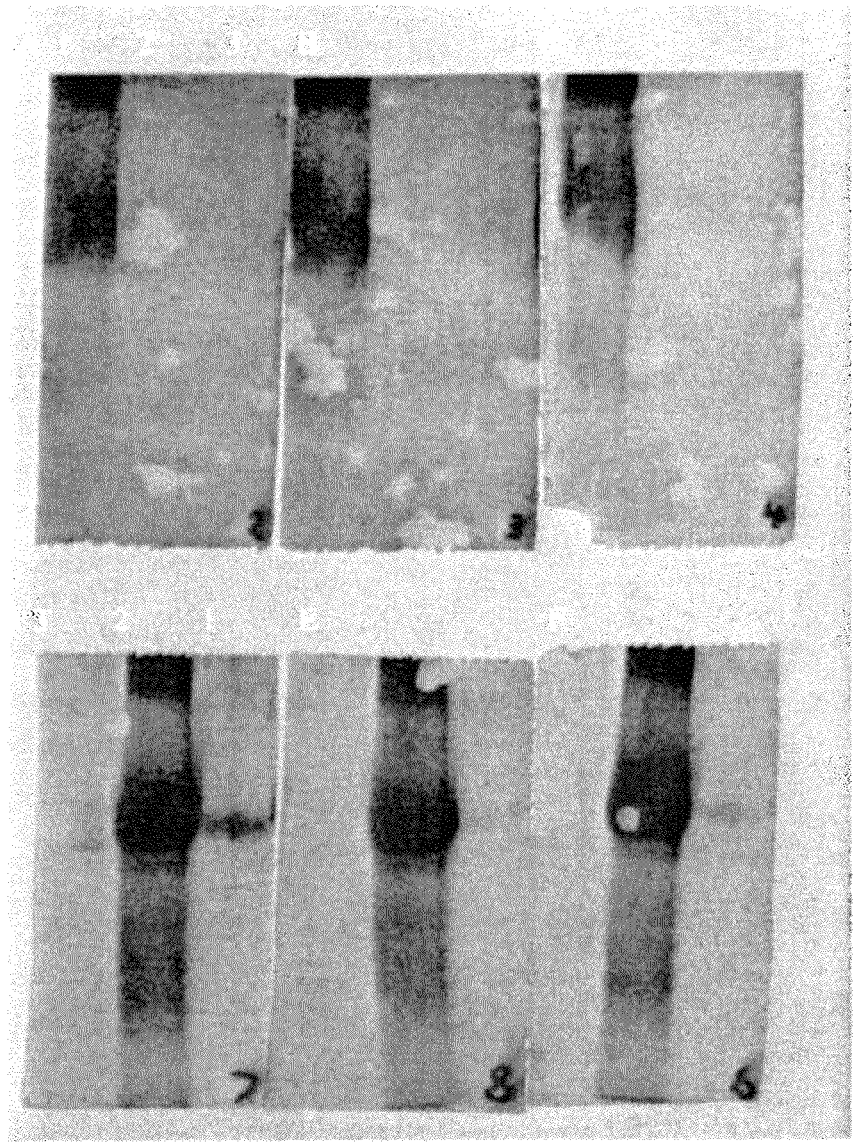
FIG. 4 shows an image of an immunoblot of BSA-BMAA conjugates probed with antisera raised against KLH-BMAA conjugates, where Lane 1 of each blot contains BSA-GLU-BMAA (BGB), Lane 2 of each blot contains BSA-EDC-BMAA (BEB), Lane 3 of each blot contains native BSA, and where Blot A is probed with anti-KGB antiserum at 1/100 dilution; Blot B is probed with anti-KGB antiserum at 1/200 dilution; Blot C is probed with anti-KGB antiserum at 1/500 dilution, Blot D is probed with anti-KEB antiserum at 1/100 dilution, Blot E is probed with anti-KEB antiserum at 1/200 dilution, Blot F is probed with anti-KEB antiserum at 1/500 dilution.

For immunoblot analysis, membranes were removed from the transfer unit (or, removed from Ponceau S de-staining solution if appropriate), and incubated in 0.1% dry milk powder (Marvel brand)/PBST for 1 hour. Membranes were then washed three times, for 5 minutes per wash (3×5) with PBST. As needed, nitrocellulose membranes were cut into strips corresponding to sample lanes. Membranes were incubated with primary antibody at various dilutions for 2 h, and then washed three times, for 5 minutes per wash (3×5) with PBST. In the experiments described herein, anti-KGB antiserum, bleed 9 (GLU 9 AS) and anti-KEB antiserum, second EDC rabbit, bleed 6 (EDC6 AS), at dilutions of 1/100, 1/200, and 1/500, were used as primary antibodies. For secondary antibody labelling, membranes were incubated with IgG-HRP (1:250) for 2 hours, and then washed three times, for 5 minutes per wash (3×5) with PBST. Peroxidase substrate was prepared by mixing a solution of 15 mg 4-chloronapthol in 5 ml cold methanol, and a solution of 15 µl $H_2O_2$ in 25 ml PBS. To visualize antibody binding, chromogenic peroxidase substrate was prepared by mixing the two solutions together and applying them to washed membranes. The reaction was monitored as bands were allowed to develop (usually approximately 5-10 minutes). Further development was stopped by addition of water. Membranes (whole membranes and/or strips) were then blotted dry The results from Ponceau S staining of nitrocellulose membranes to visualize all the transferred BSA-containing proteins on a membrane, were compared with immunoblot (Western blot) results showing antibody binding to the transferred proteins on same membrane. Results from Western blots showed similarities and differences with the Ponceau blots. When anti-KGB antiserum (bleed 9, Glu 9 AS) was used as the primary antibody to probe blots, all strengths of the antiserum preparation (1/100, 1/200, and 1/500 dilutions) appeared to react with the BGB sample (FIG. 4, Lane 1 of Blots A, B, and C), and did not appear to react with the BEB sample (FIG. 4, Lane 2 of Blots A, B, and C) or native BSA (FIG. 4, Lane 3 of Blots A, B, and C). With anti-KGB antiserum, the BGB conjugate showed antibody staining that was consistent with the Ponceau staining previously observed for the sample, where BGB samples showed intense staining of bands at positions corresponding to 191, 85 and 70 kDa (FIG. 4, Lane 1 of Blots A, B, and C). The lack of reactivity with the native BSA controls indicates that the reactivity of the anti-KGB antiserum was specific for BMAA and/or the GLU cross-linker, and was not a non-specific reactivity with BSA. The lack of reactivity with EDC cross-linked conjugate (BSA-EDC-BMAA, BEB) was difficult to interpret, as previous immunoassay results showed that anti-KGB antiserum could recognize BEB (see above), which suggested that anti-KGB antiserum might be expected to recognize epitopes on BEB on a Western blot.

When anti-KEB antiserum (bleed 6, EDC6 AS) was used as the primary antibody to probe blots, all strengths of the antiserum preparation (1/100, 1/200, 1/500) appeared to react with BEB (FIG. 4, Lane 2 of Blots D, E, and F) and BGB sample (FIG. 4, Lane 3 of Blots D, E, and F), with staining observed throughout the gel and intensely staining bands identified at positions corresponding to 191, 167, 60, 53, 35, 29, 21 and 10 kDa. Anti-KEB antiserum at 1/100 dilution showed a slight reaction with native BSA (FIG. 4, Blot D, Lane 1) while no reaction was seen at 1/200 and 1/500 dilutions (FIG. 4, Blot E, Lane 1 and Blot F, Lane 1). The reactivity of anti-KEB antiserum with both BSA-BMAA conjugates (BEB and BGB) is in accordance with previous ELISA results showing that anti-KEB antiserum could recognize both BEB and BGB (see above).

Example 8

Immunoblot Analysis of Cyanobacterial Protein Preparation from *Cylindrospermopsis raciborskii* Strain CR3

Immunoblot analysis was performed on cyanobacterial protein preparations from *Cylindrospermopsis raciborskii* strain CR3, which had previously shown to contain large amounts of cytosolic BMAA (free BMAA), in addition to BMAA in the protein fraction (protein-bound BMAA) (Cox et al. (2005) *Proc Natl Acad Sci USA* 102:5074-5078). *Cylindrospermopsis raciborskii* strain CR3 ("CR3") was harvested from mass culture at the University of Dundee and prepared as follows. A sample of 175 ml of late log phase culture of the filamentous cyanobacterium was removed and the gas vacuoles were collapsed by mechanical shock (banging full centrifuge tubes on the bench). The filaments were centrifuged for 10 minutes at 3500 rpm (Heraeus Labofuge 400). The supernatant was removed and the pellets were resuspended and transferred to 1.5 ml microcentrifuge tubes for further centrifugation at 4000 rpm (2.5 minutes, Eppendorf centrifuge 5415D). The supernatant was again removed and the pellets were resuspended in 50 mM Tris buffer at pH 7.5 to a final volume of 1 ml. The suspension was ultrasonicated on ice for approximately 1 minute to disrupt cells and release proteins. The suspension was again centrifuged and the protein concentration of the supernatant was analyzed using a dye-binding protein reagent (Sigma) and measuring absorbance at 595 nm (Bradford, 1976, *Anal Biochem* 72:248-254). The supernatant was then modified by addition of EDTA to a final concentration of 1 mM and glycerol to a concentration of 10% (v/v).

Prior to electrophoresis and immunoblot analysis, some samples of the CR3 protein preparation were pre-incubated with free BMAA ("spiked" with BMAA), to prepare samples to test whether BMAA would react with any proteins present in the cyanobacterial protein preparation. Native BSA was used as a control.

Figure 5:
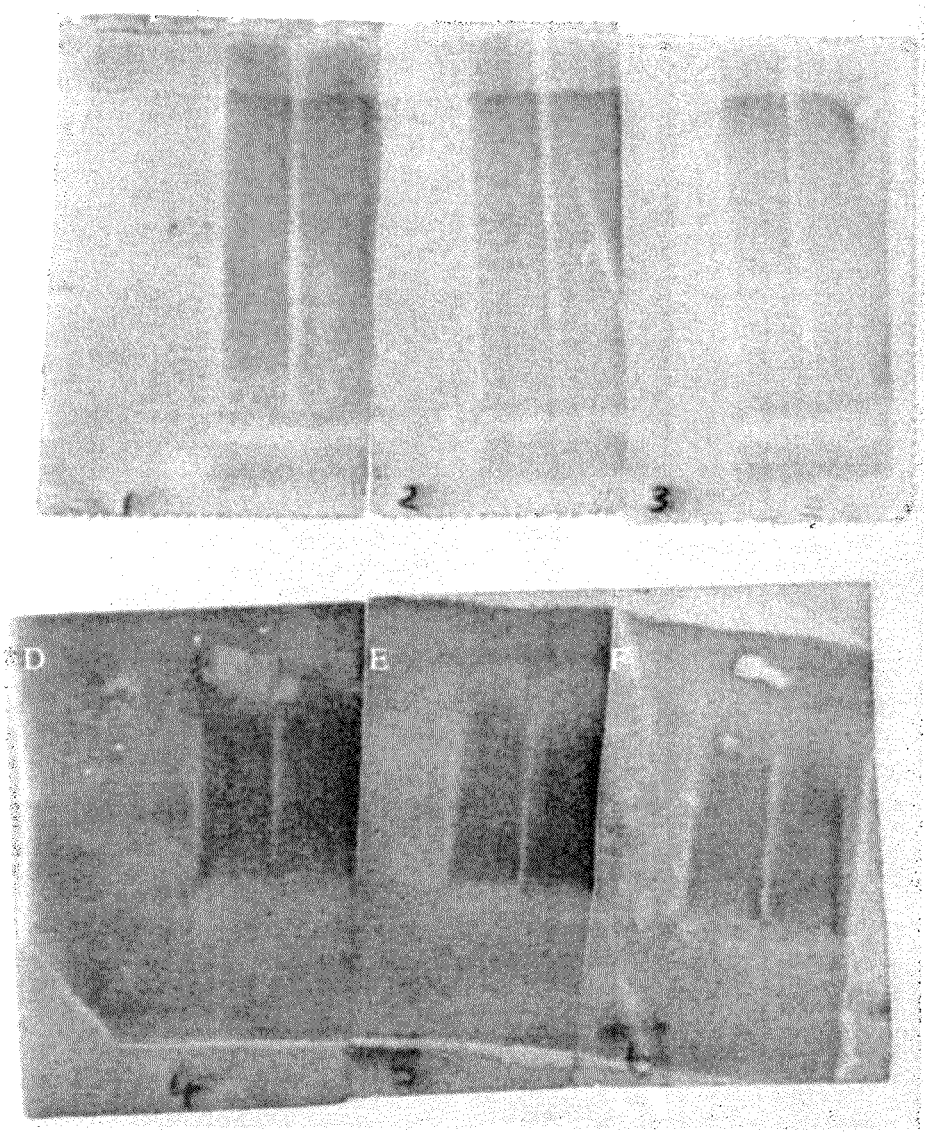
FIG. 5 shows an image of an immunoblot of total protein extracts of *Cylindrospermopsis raciborskii* strain CR3 ("CR3 protein") probed with antisera raised against BMAA conjugates, where Lane 1 of each blot contains BSA, Lane 2 of each blot contains CR3 protein, and Lane 3 of each blot contains CR3 protein pre-incubated with BMAA, and where Blot A was probed with anti-KGB antiserum at 1/100 dilution, Blot B was probed with anti-KGB antiserum at 1/200 dilution, Blot C was probed with anti-KGB antiserum at 1/500 dilution, Blot D was probed with anti-KEB antiserum at 1/100 dilution, Blot E was probed with anti-KEB antiserum at 1/200 dilution, and Blot F was probed with anti-KEB antiserum at 1/500 dilution.

SDS-PAGE was performed as described above, with 28 µg protein (28 µg CR3 total protein extract) loaded per lane, 4% stacking and 12% separating gel, and transfer to nitrocellulose membranes. After proteins were transferred to nitrocellulose membranes, anti-KGB antiserum (bleed 9, KGB9) and anti-KEB antiserum (bleed 6, KEB6) were used as primary antibodies to probe Western blots of CR3 proteins. As shown in FIG. 5, both anti-KGB and anti-KEB antisera reacted with one or more epitopes on proteins in the CR3 protein preparation (Lane 2, all blots). Although both antisera reacted with CR3 proteins, the reaction profiles differed. Anti-KGB antiserum reacted with proteins having molecular weights ranging from 10 to 120 kDa. Anti-KEB antiserum reacted with protein having molecular weights ranging from 21 to 196 kDa. Pre-incubating ("spiking") the CR3 protein preparation with free BMAA had no detectable effect on antiserum reactivity (Lane 3, all blots). These results indicated that the CR3 cyanobacterial protein preparation contained proteins with epitopes that are recognized by anti-BMAA antisera.

BSA controls showed slight reactivity with both antisera at the highest antiserum dilution tested (1/100), although this reactivity was not seen when the antiserum concentration was decreased. This result indicated some nonspecific binding to BSA when the primary antibody was present at higher concentrations (FIG. 5, Lane 1, all blots).

Example 9

Tests of Non-Specific Reactivity on Immunoblots

Figure 6:
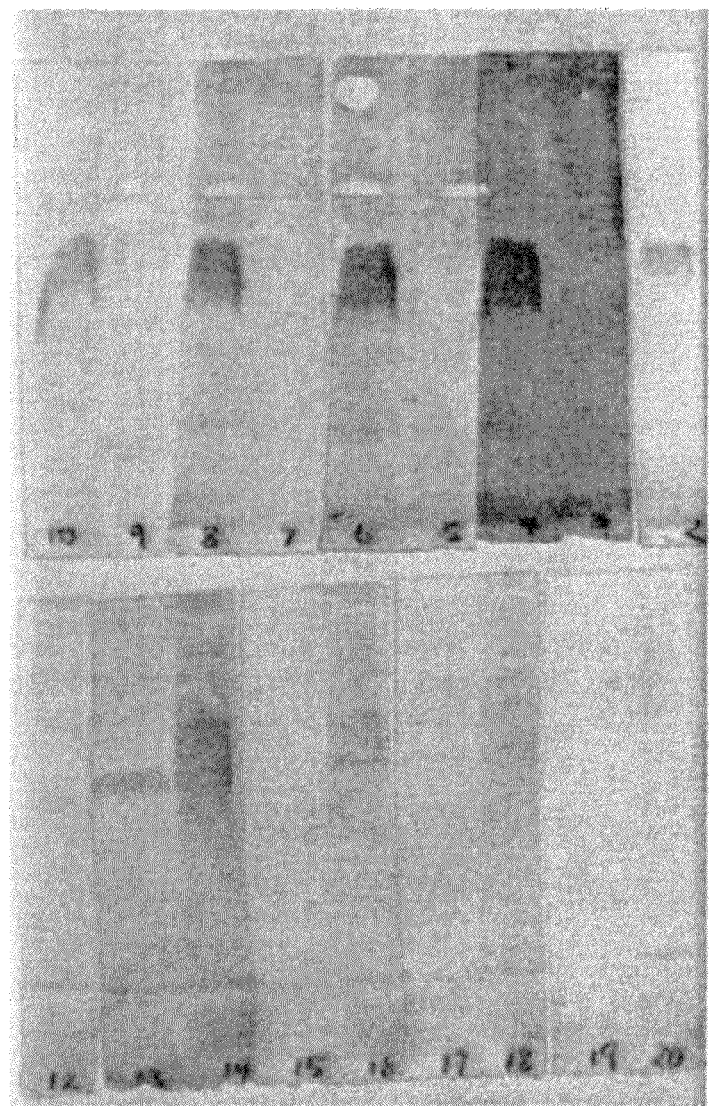
FIG. 6 shows an image of an immunoblot of total protein extracts of *C. raciborskii* strain CR3 ("CR3 protein"), and side-by-side BSA controls, probed with antisera raised against BMAA conjugates, where odd-numbered lanes contain native BSA and even-numbered lanes contain CR3 total protein, where Lanes 3-10 were probed with anti-KGB antiserum, Lanes 12-10 were probed with anti-KEB antiserum, and Lanes 2 and 12 were probed with null serum as follows: Lane 2, CR3 protein probed with null serum at 1/200 dilution.

In order to test the possibility that some of reactivity observed on immunoblots (see above) was due to non-specific reactivity, immunoblot analysis was carried out using lower dilutions of antisera raised against BMAA (anti-KGB and anti-KEB), and null (pre-immune) serum (FIG. 6). Samples of *Cylindrospermopsis raciborskii* strain CR3 ("CR3") extracts and native BSA were evaluated for nonspecific reactivity. For SDS-PAGE, 28 µg protein (CR3 total protein extract) or 10 µg BSA was loaded in each lane, and the gel composition, running conditions, transfer conditions and immunoblot conditions were as described above.

Anti-KGB antiserum (KGB9) was used as a primary antibody at dilutions of 1/200, 1/500, 1/1000, and 1/2000. Anti-KEB antiserum (EDC6) was used as a primary antibody at dilutions of 1/200, 1/500, 1/1000, and 1/2000. Null serum (NS) collected from a rabbit prior to immunization was used as a primary antibody at a dilution of 1/200.

Both antisera, at all dilutions, showed reactivity with proteins in the CR3 extract and very slight reactivity with the BSA samples. Comparison of the reactivity patterns seen for anti-KGB and anti-KEB antisera showed that anti-KEB antiserum reacted with a greater number of protein bands, and the staining of these based was more distinct, whereas anti-KGB antiserum appeared to react with only one protein complex. Anti-KEB antiserum, at all dilutions, reacted with CR3 proteins in a region corresponding to an average molecular weight of about 66 kDa, with distinct bands visible on the blot. Anti-KEB antiserum at 1/200 dilution showed reactivity with BSA in a region corresponding to a molecular weight of between about 54 and 66 kDa. Anti-KGB antiserum showed strong reactivity with CR3 proteins in a region corresponding to an average molecular weight of about 50 kDa. Null serum also showed reactivity with CR3 proteins in the same region, corresponding to an average molecular weight of about 50 kDa.

In the CR3 extracts, the NS reacted with a band of between 50 and 60 kDa (Lanes 2, 12). However, when the intensity of staining was compared, it was clear that the anti-KGB antiserum showed a significantly higher staining intensity and recognized a greater number of protein bands in the CR3 sample. This difference was also seen when the results from anti-KEB antiserum and the null serum (NS) were compared, although the contrast is less dramatic. In this experiment, the null serum (NS) was collected from one rabbit, as previous experiments with null serum had not shown any differences between null serum taken from different rabbits prior to immunization with different BMAA conjugates, such that there were no previous indications of any rabbit-specific reactivity with BMAA or BMAA conjugates. In light of these results, null serum (NS) was used as a control indicator for Western blots, such that the color development reaction was stopped when bands begin to appear in the membrane incubated with the null serum (NS) control. That is, when bands begin to appear in the sample probed with NS, the color development reaction is stopped because it is understood that specific reactions have probably reached completion and any further color development is probably due to nonspecific reactions.

Because anti-KEB antisera appeared to react with a greater variety of CR3 protein bands, and the bands were more defined than the anti-KGB-reactive proteins, it was decided that anti-KEB antiserum would be used at more dilutions than anti-KGB antiserum in the analyses described below. Furthermore, because the use of more concentrated antiserum solutions (e.g., dilutions of 1/100) appeared to result in increased non-specific binding, lower concentrations (higher dilutions) of primary antibody were used in the analyses described below, to improve the likelihood of specific detection of BMAA-containing proteins.

Example 10

Immunoblot Analysis of Protein Preparations from Other Cyanobacterial Strains

Protein extracts were prepared from additional cyanobacterial strains for immunoblot analysis using anti-KGB and anti-KEB antisera, in order to compare protein profiles and antiserum reactivity. Total protein extracts were prepared from *Microcystis* strain PCC7820, *Spirulina* strain PCC8005, and Baltic *Nodularia*. Protein preparations from *Cylindrospermopsis raciborskii* strain CR3 ("CR3") were included in the analysis for comparison and as positive controls. Samples from each strain were loaded (29 µg protein/lane) on a gel for SDS-PAGE, and the gel composition (e.g. 4% stacking, 12% separating), running conditions, transfer conditions and immunoblot conditions were as described above.

SDS-PAGE gels were stained for protein using Coomassie stain to show the protein profile for each cyanobacterial protein preparation. When SDS gels were stained with the more sensitive silver nitrate stain and compared with the less sensitive Coomassie Blue, additional protein bands were seen, indicating the presence of a wide variety of proteins in the extracts that were not visible with Coomassie staining but were potentially detectable by immunoblot (Western blot) analysis. After proteins were transferred from SDS-PAGE gels to a nitrocellulose membrane, efficiency of protein transfer was assessed by reversibly staining the membranes with Ponceau S to visualize proteins. SDS-PAGE gels were tested for protein before and after transfer, to confirm that protein had been present in the gel (before) and had been transferred out of the gel (after) to the nitrocellulose membrane.

Blots of the four cyanobacterial protein extracts were probed with anti-KEB antiserum and anti-KGB antiserum to determine whether antisera raised against BMAA conjugates would react with proteins in these extracts, and to indirectly explore whether any specific cyanobacterial proteins appeared to be BMAA-associated. Blots of the four cyanobacterial protein extracts were also probed with null serum (NS) to test for non-specific reactivity. Staining patterns and results from protein stains and immunoblots were compared.

When immunoblots probed with anti-BMAA antisera were compared with immunoblots probed with null serum, the reactions seen with anti-BMAA antisera showed a different pattern and much higher signal intensity. The intensity of the reaction of anti-BMAA antisera with the cyanobacterial protein preparations was different for each strain, with *Cylindrospermopsis raciborskii* CR3 showing the most intense (darkest color) reaction, with *Microcystis* PCC7820 next in intensity, followed by *Spirulina* PCC8005, and the least intense (lightest color) reaction was seen with the Baltic *Nodularia*. When immunoblots were probed with null serum, a band corresponding to a protein having a molecular weight of about 59 kDa was observed. When immunoblots were probed anti-BMAA antisera, bands were labelled in each strain as follows. For CR3, bands corresponding to proteins having molecular weights of about 243, 149, 129, and 114 KDa were labelled, and a "smear" corresponding to proteins having molecular weights from about 42 to 104 kDa was labelled. For PCC8005, bands corresponding to proteins having molecular weights of about 249, 129, 44 and 29 kDa were labelled. For Baltic *Nodularia*, bands corresponding to proteins having molecular weights of about 136, 123, 44 and 30 kDa were labelled. For PCC7820, a "smear" corresponding to proteins having molecular weights from about 69 to 106 kDa was labelled.

Example 11

Reactivity of Anti-BMAA Antisera with Commercially Available Organisms

Because cyanobacteria showed strain-specific differences in reactivity of anti-BMAA antisera (see above), other organisms were assessed by immunoblot analysis to ascertain their potential reactivity with the anti-BMAA antisera. Commercially available supplements of baker's yeast (*Saccharomyces cerevisiae*) and "green algae" (*Chlorella* sp.) dietary supplements were tested for their reactivity with the anti-BMAA antisera by immunoblotting. Protein preparations from *Chlorella* dietary supplements reacted strongly with the anti- BMAA antisera and the baker's yeast (*Saccharomyces cerevisiae*) preparations showed slight reactivity.

Example 12

Reactivity of Anti-BMAA Antisera with *E. coli*, *Tetraselmis*, and *Chlorella*

As the provenance of the commercial products tested above could not be established, further studies were carried out using pure strains with known history. Furthermore, these pure strains of certain organisms were tested as possible "negative controls" for comparison with cyanobacteria. Pure strains of *Escherichia coli* (strain HK29; Dr. H. K. Young, University of Dundee), the green alga *Chlorella vulgaris* and the green alga *Tetraselmis* sp. were obtained, as possible negative controls, so that the circumstances of possible BMAA association with cyanobacteria would be better understood.

Pure strains of *Escherichia coli* (strain HK29), *Chlorella vulgaris* and *Tetraselmis* sp. were obtained and harvested, and total protein extracts were prepared. Samples from each strain were loaded on a gel (29 μg protein/lane) for SDS-PAGE, and the gel composition (e.g. 4% stacking, 12% separating), running conditions, transfer conditions and immunoblot conditions were as described above. Protein preparations of *Cylindrospermopsis raciborskii* CR3 were included for comparison.

As shown in FIG. 7, the expected pattern of reactivity with CR3 protein samples was seen, and the protein samples from other organisms showed some reactivity with the antisera used to probe the blots. Neither anti-KEB antiserum at 1/500 or 1/1000, nor anti-KGB antiserum at 1/500 (the only dilution tested) showed detectable reactivity with any proteins of either of the green algae, *Chlorella* and *Tetraselmis*.

Anti-KEB antiserum (EDC 6 AS) at 1/500 dilution, labelled bands in the CR3 sample corresponding to proteins having molecular weights of about 124, 89, 59 and 35 kDa (FIG. 7, Lane 6) and at 1/1000 dilution, anti-KEB antiserum labelled bands in the CR3 corresponding to proteins having molecular weights of about 121, 94, 79 kDa (FIG. 7, Lane 12). Anti-KEB antiserum at 1/500 showed strong labelling of bands in the *E. coli* sample, corresponding to proteins having molecular weights of about 124, 97, 86, 79, 73, 59, 50, 46, 38, 35, 27, 24, 22, 16, 12, 11 and 9 kDa (FIG. 7, Lane 7). At 1/1000 dilution, anti-KEB antiserum weakly labelled bands in the *E. coli* sample, corresponding to proteins having molecular weights of about 109, 98, 88, 61, 48, 43, 38, 27, 25, 23, 16, 14, 13 and 9 kDa, although the bands were labelled with much less intensity than with the antiserum at 1/500 (FIG. 7, Lane 13).

Anti-KGB antiserum at 1/500 dilution labelled bands in the CR3 sample in a "smear" corresponding to proteins having molecular weights ranging from about 84 to 36 kDa (FIG. 7, Lane 16). Anti-KGB antiserum at 1/500 dilution showed strong labelling of bands in the *E. coli* sample, corresponding to proteins having molecular weights of about 66, 58, 49, 44 and 24 kDa (FIG. 7, Lane 17).

Null serum (at 1/500 dilution) showed little reactivity with CR3 (FIG. 7, Lane 2). In the *E. coli* sample, null serum labelled bands corresponding to proteins having molecular weights of about 91, 13 and 12 kDa (FIG. 7, Lane 3). In *Chlorella*, null serum labelled a band corresponding to a protein having a molecular weight of about 11 kDa (FIG. 7, Lane 4). In *Tetraselmis*, null serum labelled a band corresponding to a protein having a molecular weight of about 10 kDa (FIG. 7, Lane 5).

The reactivity of anti-KEB and anti-KGB antisera with proteins of *E. coli* strain HK29 was stronger than the reactivity of the antisera with proteins of any of the cyanobacterial strains previously tested, when the same amount of total protein extract was loaded in each lane. A wide range of specific protein bands in the *E. coli* preparation were stained by both antisera. Samples of *E. coli* strain HK29 were harvested and freeze-dried for BMAA analysis by HPLC.

Because denaturing SDS-PAGE was used to separate proteins from all the organisms tested above, and because anti-KGB and anti-KEB antisera labelled various distinct protein bands on immunoblots separated denatured proteins from various organisms, the experiments above suggested that BMAA was incorporated into polypeptide chains, both as demonstrated by the analysis of reactivity with synthetic immunoconjugates, and as demonstrated by the results showing that antisera raised against BMAA conjugates were reactive with protein extracts from living organisms.

Various modifications can be made to the preferred embodiments without departing from the spirit and scope of the invention as defined in the appended claims.

What is claimed is:

1. A method for screening a sample to detect the presence of β-N-methylamino-L-alanine (BMAA), comprising contacting the sample with an antibody that binds to L-isomer of BMAA and does not substantially bind to D-isomer of BMAA, and detecting the antibody that binds to the L-isomer of BMAA and does not substantially bind to the D-isomer of BMAA.

2. The method of claim 1, comprising screening a tissue sample from a subject to detect the presence of BMAA in the tissue sample, wherein the presence of a detectable amount of BMAA in the sample indicates exposure of the subject to an environmental source of BMAA.

3. The method of claim 2, wherein the tissue sample is neurological tissue.

4. The method of claim 2, wherein the tissue sample is non-neurological tissue.

5. The method of claim 4, wherein the non-neurological tissue is keratinous tissue.

6. The method of claim 5, wherein the keratinous tissue is hair.

7. The method of claim 5, wherein the keratinous tissue is skin.

8. The method of claim 5, wherein the keratinous tissue is nail, claw, or hoof.

9. The method of claim 5, comprising detecting the presence of protein-bound BMAA on an immunoblot of the tissue sample.

10. The method of claim 1, wherein the sample is an environmental sample.

11. The method of claim 10, wherein the environmental sample is a water sample.

12. The method of claim 10, wherein the environmental sample is from a food item.

13. The method of claim 10, further comprising screening the sample to detect cyanobacterial material in the sample.

14. The method of claim 10, comprising detecting the presence of protein-bound BMAA on an immunoblot of the environmental sample, and further comprising detecting cyanobacterial proteins on the immunoblot.

15. An antibody that binds to the L-isomer of BMAA and does not substantially bind the D-isomer of BMAA.

16. An antibody of claim 15, that does not substantially bind to an amino acid selected from the group consisting of L-alanine, L-glutamine, L-tyrosine, glycyl-glycine, L-glycine, L-leucine, L-phenylalanine, gamma-aminobutyric acid (GABA), L-glutamic acid, and L-aspartic acid.

17. The antibody of claim 15, wherein the antibody binds to free BMAA.

18. The antibody of claim 15, wherein the antibody binds to protein-bound BMAA.

19. The antibody of claim 15, wherein the antibody binds to both free BMAA and protein-bound.

20. The antibody of claim 15, wherein the antibody is a polyclonal antibody.

21. The antibody of claim 15, wherein the antibody is a monoclonal antibody.

22. The antibody of claim 15, wherein the antibody is an antibody fragment.

23. The antibody of claim 15, wherein the antibody is detectably labelled.

24. The antibody of claim 15, wherein the antibody is labelled for use in in vivo diagnostic imaging.

25. The method of claim 1, wherein protein-bound BMAA is detected.

26. The method of claim 1, wherein both free BMAA and protein-bound BMAA is detected.

27. The method of claim 1, wherein the method comprises an enzyme-linked immunosorbent assay (ELISA).

28. The method of claim 27, wherein the ELISA is an antibody capture assay.

29. The method of claim 27, wherein the ELISA is an indirect competitive ELISA.

30. The method of claim 27, wherein the ELISA is a direct ELISA.

31. The method of claim 1, wherein the method comprises an immunoblot assay.

32. The method of claim 1, wherein the antibody that binds to L-isomer of BMAA does not substantially bind to an amino acid selected from the group consisting of L-alanine, L-glutamine, L-tyrosine, glycyl-glycine, L-glycine, L-leucine, L-phenylalanine, gamma-aminobutyric acid (GABA), L-glutamic acid, and L-aspartic acid.

33. The method of claim 1, wherein the antibody that binds to L-isomer of BMAA comprises a polyclonal antibody.

34. The method of claim 1, wherein the antibody that binds to L-isomer of BMAA comprises a monoclonal antibody.

35. The method of claim 1, wherein the antibody that binds to L-isomer of BMAA comprises an antibody fragment.

36. The method of claim 1, wherein the antibody that binds to L-isomer of BMAA is detectably labelled.

37. The method of claim 1, wherein the antibody is labelled with a label selected from the group consisting of: a radiolabel, a fluorescent moiety, a luminescent moiety, a chemiluminescent moiety, a colloidal gold label, a dye moiety, a paramagnetic compound, a detectable enzyme, biotin, avidin, and streptavidin.

38. The method of claim 1, wherein the antibody that binds to L-isomer of BMAA is not detectably labelled, and further comprising a detectably labelled secondary antibody that binds to the antibody that binds to L-isomer of BMAA.

39. The method of claim 38, wherein the secondary antibody is labelled with a label selected from the group consisting of: a radiolabel, a fluorescent moiety, a luminescent moiety, a chemiluminescent moiety, a colloidal gold label, a dye moiety, a detectable enzyme, a detectable ligand, biotin, avidin, and streptavidin.

40. The method of claim 38, wherein the secondary antibody is labelled with a detectable enzyme.

41. The method of claim 40, wherein the detectable enzyme is horseradish peroxidase (HRP).

42. The method of claim 1, further comprising an amplification step.

* * * * *